US011117872B2

(12) United States Patent
Shimono et al.

(10) Patent No.: US 11,117,872 B2
(45) Date of Patent: Sep. 14, 2021

(54) OXAZINE COMPOUND, COMPOSITION AND CURED PRODUCT

(71) Applicant: DIC Corporation, Tokyo (JP)

(72) Inventors: Tomohiro Shimono, Sakura (JP); Kazuo Arita, Sakura (JP); Junji Yamaguchi, Sakura (JP); Masato Otsu, Sakura (JP)

(73) Assignee: DIC Corporation, Tokyo (JP)

( * ) Notice: Subject to any disclaimer, the term of this patent is extended or adjusted under 35 U.S.C. 154(b) by 439 days.

(21) Appl. No.: 15/781,818

(22) PCT Filed: Nov. 24, 2016

(86) PCT No.: PCT/JP2016/084728
§ 371 (c)(1),
(2) Date: Jun. 6, 2018

(87) PCT Pub. No.: WO2017/098926
PCT Pub. Date: Jun. 15, 2017

(65) Prior Publication Data
US 2018/0362478 A1 Dec. 20, 2018

(30) Foreign Application Priority Data
Dec. 8, 2015 (JP) .............................. JP2015-239363

(51) Int. Cl.
C07D 265/16 (2006.01)
C08J 5/24 (2006.01)
H05K 1/03 (2006.01)
H01L 23/29 (2006.01)
H01L 23/31 (2006.01)
B32B 15/08 (2006.01)
H05K 1/09 (2006.01)

(52) U.S. Cl.
CPC ............ C07D 265/16 (2013.01); B32B 15/08 (2013.01); C08J 5/24 (2013.01); H01L 23/29 (2013.01); H01L 23/31 (2013.01); H05K 1/03 (2013.01); H05K 1/0373 (2013.01); H05K 1/09 (2013.01); H01L 23/295 (2013.01)

(58) Field of Classification Search
CPC ...... C07D 265/16; C07D 265/14; H05K 1/03; H05K 1/0373; H05K 1/09; H01L 23/29; H01L 23/31; H01L 23/295; B32B 15/08; C08J 5/24; C08K 7/02
See application file for complete search history.

(56) References Cited

U.S. PATENT DOCUMENTS

| 2006/0240261 A1 | 10/2006 | Helen Li et al. |
| 2009/0215943 A1 | 8/2009 | Hirose et al. |
| 2011/0056779 A1* | 3/2011 | McGee ............... F16D 69/04 188/250 E |
| 2018/0333941 A1 | 11/2018 | Otsu et al. |

FOREIGN PATENT DOCUMENTS

| CN | 101935453 A | 1/2011 |
| CN | 102250117 A | 11/2011 |
| CN | 103936686 A | 7/2014 |
| JP | 11-012258 A | 1/1999 |
| JP | 2000-169456 A | 6/2000 |
| JP | 2009-262227 A | 11/2009 |
| WO | 2006/062891 A1 | 6/2006 |
| WO | 2009/123285 A1 | 10/2009 |
| WO | 2017/104294 A1 | 6/2017 |

OTHER PUBLICATIONS

Akira et al, Nov. 2009, Google translation for WO 2009/123285 A1 (Year: 2009).*
International Search Report dated Jan. 31, 2017, issued for PCT/JP2016/084728.
Xin Huang et al.; "Greatly Enhanced Thermo-oxidative Stability of Polybenzoxazine Thermoset by Incorporation of m-Carborane", Journal of Polymer Science, Part A: Polymer Chemistry, vol. 53, No. 8, Apr. 15, 2015, pp. 973-980. (cited in the Apr. 23, 2019 Search Report for EP 16872826.9).
Kubra Dogan Demir et al., "Thermally Curable Acetylene-Containing Main-Chain Benzoxazine Polymers via Sonogashira Coupling Reaction," Macromolecules, vol. 44, No. 7, Apr. 13, 2011, pp. 1801-1807. (cited in the Apr. 23, 2019 Search Report for EP 16872826.9).
Supplementary European Search Report dated Apr. 23, 2019, issued for the European patent application No. 16872826.9.
Notice of Reason for Refusal dated Aug. 31, 2017, issued for the Japanese patent application No. 2017-539687 and English translation thereof.

* cited by examiner

Primary Examiner — Nathan L Van Sell
(74) Attorney, Agent, or Firm — Locke Lord LLP; James E. Armstrong, IV; Nicholas J. DiCeglie, Jr.

(57) ABSTRACT

The present invention provides an oxazine compound having a specific structure, which contains a group having an aromatic ring structure and a plurality of specified carbon-carbon triple bond structure. The present invention further provides a composition containing the oxazine compound having a specific structure of the present invention, a cured product containing the composition, and a laminate having the layer of the cured product. The present invention further still provides a composition for a heat-resistant material and a composition for an electronic material, which contain the composition containing the oxazine compound of the present invention.

17 Claims, No Drawings

OXAZINE COMPOUND, COMPOSITION AND CURED PRODUCT

TECHNICAL FIELD

The present invention relates to an oxazine compound excellent in heat resistance, dielectric properties, and low hygroscopicity, a composition, a cured product, and a laminate each containing the oxazine compound. The present invention further relates to a heat-resistant material and a heat-resistant member, and an electronic material and an electronic member each containing the oxazine compound.

BACKGROUND ART

Various resins such as an epoxy resin, a cyanate ester resin, a bismaleimide-triazine resin, and a benzoxazine resin have been used as a resin material for an electronic component used for a semiconductor sealing material and an insulating layer for a multilayer printed board, and in recent years, in various applications, particularly in most-advanced electronic materials applications, materials and compositions which realize further improvement in performance such as heat resistance and dielectric properties and exhibit low moisture absorptivity have been required.

Among them, benzoxazine, which can be easily prepared by combining a phenol compound, an amine compound, and formaldehyde, undergoes ring-opening polymerization by heating by itself, and exhibits high heat resistance and low linear expansion due to a strong hydrogen bonding structure formed in a crosslinked structure. From this reason, nawadays, the benzoxazine is not only examined for the above-mentioned application of electric materials, but also attracts attention as a resin material for next generation devices typified by SiC power semiconductors.

As benzoxazine in the related art, benzoxazines prepared from a bifunctional phenol such as bisphenol F and bisphenol A and aniline are disclosed in PTL 1 and PTL 2. However, since an aniline-derived component is generated as a decomposed gas at the time of ring-opening of oxazine, the thermal decomposition resistance which is an index of long-term thermal durability has not reached a level required in recent years, and thus further improvement and performance improvement are strongly desired.

CITATION LIST

Patent Literature

[PTL 1] JP-A-11-12258
[PTL 2] JP-A-2000-169456

SUMMARY OF INVENTION

Technical Problem

An object of the present invention is to provide a novel oxazine compound which is excellent in thermal decomposition resistance and excellent in dielectric properties and low hygroscopicity. Another object of the present invention is to provide a composition containing the novel oxazine compound, a cured product, and a laminate containing the cured product. Still another object of the present invention is to provide a heat-resistant material and an electronic material which contain the novel oxazine compound.

Solution to Problem

As a result of intensive studies, the inventors of the present invention have found that an oxazine compound containing a group having an aromatic ring structure and a plurality of specified carbon-carbon triple bond structures achieves the above objects.

That is, the present invention provides an oxazine compound which has a structure of General Formula (1) in which General Formula (1) has at least two or more functional groups $R^1$ represented by General Formulae (4) and (5) so as to achieve the above objects.

[Chem. 1]

$$X\text{-}(Y)_n \quad (1)$$

(In Formula (1), n represents an integer of 2 to 4, Y's each independently represents a structure represented by General Formula (2), and X is represented by any one of General Formulae (3).)

[Chem. 2]

$$a^1\text{-}N\text{-}\underset{O}{\overset{A}{\diagup}} \quad (2)$$

(In Formula (2), a ring A represents a substituted or unsubstituted aromatic ring, and $a^1$ represents a bonding position to X in General Formula (1).)

[Chem. 3]

$$\quad (3)$$

$$Ar^1 \quad (3\text{-}1)$$

$$Ar^2\text{—}Ar^3 \quad (3\text{-}2)$$

$$Z^1\text{-}(Ar^4)_{n2} \quad (3\text{-}3)$$

$$Ar^5\text{-}(Z^2\text{—}Ar^7)_{n3}\text{-}Z^3\text{—}Ar^6 \quad (3\text{-}4)$$

(In Formula (3), $Ar^1$ to $Ar^6$ each independently represent a substituted or unsubstituted aryl group, $Ar^7$ represents a substituted or unsubstituted arylene group, $n^2$ represents an integer of 2 to 4, $n^3$ represents 1 or 2, $Z^1$, $Z^2$, and $Z^3$ each independently represent a single bond, a nitrogen atom, an oxygen atom, an alkylene group, an arylene group, a carbonyl group, an ester group, an amide group, an imino group, an azo group, a sulfide group, a sulfone group, and any one of groups obtained by combining two or more of these groups.)

[Chem. 4]

$$a^2\text{—}V^1\text{—}Q^1\text{—}V^2\text{—}{\equiv}\text{—}R^2 \quad (4)$$

(In Formula (4), $V^1$, $V^2$, and $Q^1$ each independently represent a single bond or a divalent linking group, $R^2$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^2$ represents a bonding point to General Formula (1).)

[Chem. 5]

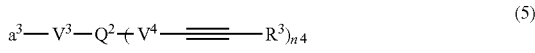
(5)

(In Formula (5), $n^4$ represents an integer of 2 to 4, $V^3$ and $V^4$ each independently represent a single bond or a divalent linking group, $Q^2$ represents a linking group having a valence of $n^4+1$, $R^3$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^3$ represents a bonding point to General Formula (1).)

The present invention further provides a composition containing the oxazine compound of the present invention, a cured product containing the composition, and a laminate having the layer of the cured product. The present invention further still provides a composition for a heat-resistant material and a composition for an electronic material, which contain a composition containing the oxazine compound of the present invention.

Advantageous Effects of Invention

The cured product of the oxazine compound of the present invention is excellent in the thermal decomposition resistance, the dielectric properties, and the low hygroscopicity, and thus it can be suitably used for a heat-resistant member and an electronic member. In particular, it can be suitably used for a semiconductor sealing material, a circuit board, a build-up film, a build-up substrate, and the like. It can also be suitably used for a matrix resin of a fiber-reinforced resin, and is particularly suitable as a prepreg with high heat resistance.

DESCRIPTION OF EMBODIMENTS

<Oxazine Compound>

An oxazine compound has a structure of General Formula (1), in which General Formula (1) has at least two or more functional groups $R^1$ represented by General Formulae (4) and (5) so as to achieve the above objects.

[Chem. 6]

$$X\text{-}(Y)_n \quad (1)$$

(In Formula (1), n represents an integer of 2 to 4, Y's each independently represents a structure represented by General Formula (2), and X is represented by any one of General Formulae (3).)

[Chem. 7]

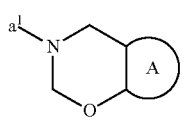
(2)

(In Formula (2), a ring A represents a substituted or unsubstituted aromatic ring, and $a^1$ represents a bonding position to X in General Formula (1).)

[Chem. 8]

$Ar^1$ (3-1)

$Ar^2\text{—}Ar^3$ (3-2)

$Z^1\text{-}(Ar^4)_{n2}$ (3-3)

$Ar^5\text{-}(Z^2\text{—}Ar^7)_{n3}\text{—}Z^3\text{—}Ar^6$ (3-4)

(In Formula (3), $Ar^1$ to $Ar^6$ each independently represent a substituted or unsubstituted aryl group, $Ar^7$ represents a substituted or unsubstituted arylene group, $n^2$ represents an integer of 2 to 4, $n^3$ represents 1 or 2, $Z^1$, $Z^2$, and $Z^3$ each independently represent a single bond, a nitrogen atom, an oxygen atom, an alkylene group, an arylene group, a carbonyl group, an ester group, an amide group, an imino group, an azo group, a sulfide group, a sulfone group, and any one of groups obtained by combining two or more of these groups.))

[Chem. 9]

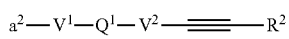
(4)

(In Formula (4), $V^1$, $V^2$, and $Q^1$ each independently represent a single bond or a divalent linking group, $R^2$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^2$ represents a bonding point to General Formula (1).)

[Chem. 10]

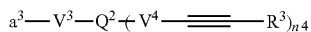
(5)

(In Formula (5), $n^4$ represents an integer of 2 to 6, $V^3$ and $V^4$ each independently represent a single bond or a divalent linking group, $Q^2$ represents a linking group having a valence of $n^4+1$, $R^3$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^3$ represents a bonding point to General Formula (1).)

In General Formula (1), a bonding moiety of the functional group $R^1$ is not particularly limited, and for example, two or more of them may be bonded to X in the formula, two or more of them may be bonded to Y, or may be bonded to each of X and Y.

As a preferable structure, a structure in which the functional group $R^1$ is bonded to Y in Formula (1) is preferable from the aspect of improving the heat resistance. Specifically, a structure represented by Formula (1-1) is exemplified.

[Chem. 11]

$X\text{-}(Y\text{—}R^1)_n$ (1-1)

(In Formula (1-1), n represents an integer of 2 to 4, $R^1$'s are each independently a group represented by Formula (4) or (5).)

Further, in addition to Y in Formula (1), a structure in which the functional group $R^1$ is bonded to X also is preferable from the viewpoint of the improvement of the heat resistance. Specifically, a structure represented by Formula (1-2) is preferable.

[Chem. 12]

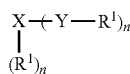
(1-2)

(In Formula (1-2), n represents an integer of 2 to 4, Y's are each independently a structure represented by General Formula (2), X is any one of General Formulae (3), and $R^1$'s each independently represent a group represented by Formula (4) or (5).)

In the oxazine compound of the present invention, a hydrogen atom of the carbon atom may be substituted. In the case of the hydrogen atom being substituted, an alkyl group having 1 to 3 carbon atoms and a substituted or unsubstituted aromatic group are preferable. The moiety where the hydrogen atom is substituted is not particularly limited.

<Functional Group $R^1$>

In the present invention, the functional group $R^1$ is a group having a carbon-carbon triple bond structure, and is, specifically, a group represented by Formula (4) or (5). In the oxazine compound of the present invention, two curing reactions, a curing reaction derived from the ring opening polymerization of the oxazine ring and a curing reaction derived from the polymerization reaction of the carbon-carbon triple bond, proceed, and thus a dense crosslinked structure is formed when cured, thereby significantly improving the heat resistance. In particular, the oxazine compound of the present invention has two or more functional groups $R^1$, and this is because the cured product forms a more dense three-dimensional crosslinking by multifunctionalization, and the heat resistance is further improved.

The functional group $R^1$ is a group represented by Formula (4) or (5), and two or more thereof are present in General Formula (1); however, the structure of the functional group $R^1$ may be different from or the same as each other.

[Chem. 13]

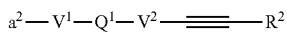
(4)

(In Formula (4), $V^1$, $V^2$, and $Q^2$ each independently represent a single bond or a divalent linking group, $R^2$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^2$ represents a bonding point to General Formula (1).)

[Chem. 14]

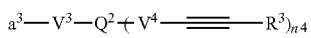
(5)

(In Formula (5), $n^4$ represents an integer of 2 to 6, $V^3$ and $V^4$ each independently represent a single bond or a divalent linking group, $Q^2$ represents a linking group having a valence of $n^4+1$, $R^3$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^3$ represents a bonding point to General Formula (1).)

As the divalent linking group in each of $V^1$, $V^2$, $V^3$, $V^4$, and $Q^1$ in Formulae (4) and (5), an oxygen atom, a divalent hydrocarbon group, or a divalent group in which one or more hydrogen atoms contained in a divalent hydrocarbon group are substituted with a hydroxyl group, an alkoxy group, or a halogen atom, a carbonyl group (—CO— group), an ester group (—COO— group), an amide group (—CONH— group), an imino group (—C=N— group), an azo group (—N=N— group), a sulfide group (—S— group), a sulfone group (—$SO_3$— group), and a divalent linking group consisting of these combinations are exemplified.

Examples of the divalent hydrocarbon group include an alkylene group, an alkenylene group, an alkynylene group, a cycloalkylene group, an arylene group, an aralkylene group (a divalent group having an alkylene group and an arylene group).

Examples of the alkylene group include a methylene group, an ethylene group, a propylene group, a butylene group, a pentylene group, and a hexylene group.

Examples of the alkenylene group include a vinylene group, a 1-methyl vinylene group, a propenylene group, a butenylene group, and a pentenylene group.

Examples of the alkynylene group include an ethynylene group, a propynylene group, a butynylene group, a pentynylene group, and a hexynylene group.

Examples of the cycloalkylene group include a cyclopropylene group, a cyclobutylene group, a cyclopentylene group, and a cyclohexylene group.

Examples of the arylene group include a phenylene group, a tolylene group, a xylylene group, and a naphthylene group.

Examples of the aralkylene group include an aralkylene group having 7 to 20 carbon atoms and having an alkylene group and an arylene group.

In the case of being a divalent group where at least one hydrogen atom contained in the hydrocarbon group is substituted with a hydroxyl group, an alkoxy group, or a halogen atom, examples thereof include a hydroxyl group-containing alkylene group, an alkoxy group-containing alkenylene group, a halogenated alkylene group, a hydroxyl group-containing alkenylene group, an alkoxy group-containing alkenylene group, a halogenated alkenylene group, a hydroxyl group-containing alkynylene group, an alkoxy group-containing alkynylene group, a halogenated alkynylene group, a hydroxyl group-containing cycloalkylene group, an alkoxy group-containing cycloalkylene group, a halogenated cycloalkylene group, a hydroxyl group-containing arylene group, an alkoxy group-containing arylene group, a halogenated arylene group, a hydroxyl group-containing aralkylene group, an alkoxy group-containing aralkylene group, and a halogenated aralkylene group.

Examples of the hydroxyl group-containing alkylene group include a hydroxyethylene group and a hydroxypropylene group. Examples of the alkoxy group-containing alkylene group include a methoxyethylene group, a methoxypropylene group, an allyloxymethylene group, an allyloxypropylene group, a propargyloxymethylene group, and a propargyloxypropylene group. Examples of the halogenated alkylene group include a chloromethylene group, a chloroethylene group, a chloropropylene group, a bromomethylene group, a bromoethylene group, a bromopropylene group, a fluoromethylene group, a fluoroethylene group, and a fluoropropylene group.

Examples of the hydroxyl group-containing alkenylene group include a hydroxybutenylene group and a hydroxypentenylene group. Examples of the alkoxy group-containing alkenylene group include a methoxybutenylene group and an ethoxyhexenylene group. Examples of the halogenated alkenylene group include a chloropropenylene group and a bromopentenylene group.

Examples of the hydroxyl group-containing alkynylene group include a hydroxypentynylene group and a hydroxyhexynylene group. Examples of the alkoxy group-containing alkynylene group include an ethoxyhexynylene group and a methoxyheptynylene group. Examples of the halogenated alkynylene group include a chlorhexynylene group and a fluorooctynylene group.

Examples of the hydroxyl group-containing cycloalkylene group include a hydroxycyclohexanylene group. Examples of the alkoxy group-containing cycloalkylene group include a methoxycyclopentanylene group. Examples of the halogenated cycloalkylene group include a dichlorocyclopentanylene group.

Examples of the hydroxyl group-containing arylene group include a hydroxyphenylene group. Examples of the alkoxy group-containing arylene group include a methoxyphenylene group, an ethoxyphenylene group, an allyloxyphenylene group, and a propargyloxyphenylene group. Examples of the halogenated arylene group include a chlorophenyl group, a bromophenyl group, a fluorophenyl group, a chloronaphthyl group, a bromonaphthyl group, and a fluoronaphthyl group.

The divalent linking group in each of $V^1$, $V^2$, $V^3$, $V^4$, and $Q^1$ in addition to the above may be an unsaturated hydrocarbon group-containing arylene group. Examples of the unsaturated hydrocarbon group-containing arylene group include vinylphenylene, allylphenylene, ethynylphenylene, and propargylphenylene.

In Formula (4), as to $Q^1$, it is preferably any one of linking groups selected from the group consisting of a single bond, an oxygen atom, an alkylene group, and an aralkylene group.

The divalent linking group in each of $V^1$, $V^2$, $V^3$, $V^4$, and $Q^1$ is preferably a single bond, a divalent hydrocarbon group, or an oxygen atom, and the divalent hydrocarbon group is preferably an alkylene group and an arylene group. As a particularly preferably combination, $V^1$ is a single bond or a phenylene group, $V^2$ is a methylene group (—CH$_2$—), $V^3$ is a single bond, $V^4$ is a methylene group (—CH$_2$—), and $Q^1$ is an oxygen atom in some cases.

In Formula (5), $Q^2$ represents a linking group having a valence of $n^4+1$. A nitrogen atom or a hydrocarbon group having 1 to 20 carbon atoms is preferable. A nitrogen atom is particularly preferable.

These linking groups may have a substituent other than a group having a carbon-carbon triple bond connected to $V^4$ (here, a bond with $V^3$ and a bond with a substituent other than a group having a carbon-carbon triple bond connected to $V^4$ are not calculated as the valence).

Specific examples of the hydrocarbon group having 1 to 20 carbon atoms in $Q^2$ include an alkylene group, an alkenylene group, a cycloalkylene group, an arylene group, and an aralkylene group.

Examples of the alkylene group include a methylene group, a methine group, an ethylene group, a propylene group, a butylene group, a pentylene group, and a hexylene group.

Examples of the alkenylene group include a vinylene group, a 1-methyl vinylene group, a propenylene group, a butenylene group, and a pentenylene group.

Examples of the alkynylene group include an ethynylene group, a propynylene group, a butynylene group, a pentynylene group, and a hexynylene group.

Examples of the cycloalkylene group include a cyclopropylene group, a cyclobutylene group, a cyclopentylene group, and a cyclohexylene group.

Examples of the arylene group include a phenylene group, a tolylene group, a xylylene group, and a naphthylene group.

Examples of the aralkylene group include an aralkylene group having an alkylene group and an arylene group and having 7 to 20 carbon atoms.

As to Formula (4), the following structures are preferably exemplified.

[Chem. 15]

(4-1)

[Chem. 16]

(4-2)

[Chem. 17]

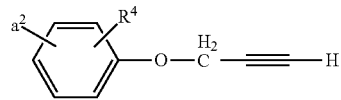

(4-3)

(In Formula (4-3), $R^4$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom.)

The case where Formula (4) is (4-2) and (4-3) having a propargyl ether group, and the case where $R^4$ is a hydrogen atom are particularly preferable. In Particular, in the case where the propargyl ether group is bonded to the aromatic ring, the propargyl ether group is expected to react to form a double bond-containing cyclic structure. When the double bond-containing cyclic structures further react with each other, a dense crosslinked structure is formed, so that the heat resistance is expected to be improved.

As to Formula (5), the following structures are preferable.

[Chem. 18]

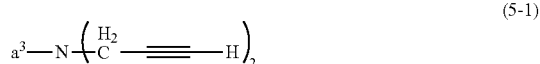

(5-1)

-continued

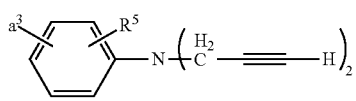
(5-2)

(In Formula (5-2), $R^5$ represents a hydrogen atom, a hydrocarbon group, or a hydrocarbon group in which one or more hydrogen atoms contained in the hydrocarbon group is substituted with any one of a hydroxyl group, an alkoxy group, and a halogen atom.)

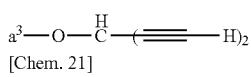
(5-3)

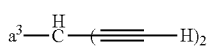
(5-4)

Formula (3) particularly preferably represents a dipropargylamino group.

<$Ar^1$ and Ring A>

In General Formula (1), Y's are each independently a structure represented by General Formula (2).

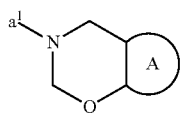
(2)

(In Formula (2), the ring A represents a substituted or unsubstituted aromatic ring, and $a^1$ represents the bonding position with X in General Formula (1).)

In General Formula (2), the ring A represents a substituted or unsubstituted aromatic ring, and specific examples of the aromatic ring include a benzene ring, a naphthalene ring, an anthracene ring, and a phenanthrene ring.

In General Formula (1), X represents any one of the structures represented by the following General formulae (3-1) to (3-4).

$Ar^1$     (3-1)

$Ar^2 — Ar^3$     (3-2)

$Z^1\!\!-\!\!(Ar^4)_{n^2}$     (3-3)

$Ar^5 —(Z^2 — Ar^7)_{n^3} Z^3 — Ar^6$     (3-4)

(In Formulae (3-1) and (3-4), $Ar^1$ to $Ar^6$ each independently represent a substituted or unsubstituted aryl group, $Ar^7$ represents a substituted or unsubstituted arylene group, $n^2$ represents an integer of 2 to 4, $n^3$ represents 1 or 2, $Z^1$, $Z^2$, and $Z^3$ each independently represent a single bond, a nitrogen atom, an oxygen atom, an alkylene group, an arylene group, a carbonyl group, an ester group, an amide group, an imino group, an azo group, a sulfide group, a sulfone group, and any one of groups obtained by combining two or more of these groups.))

As the oxazine compound of the present invention, preferable structures are compounds represented by Formulae (1-a) to (1-n).

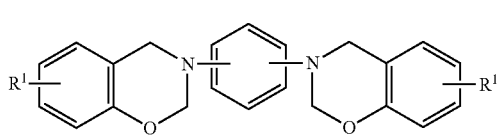
(1-a)

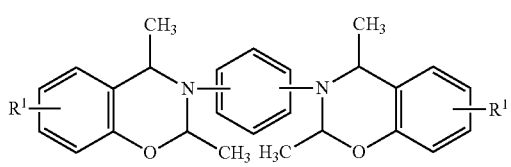
(1-b)

(1-c)

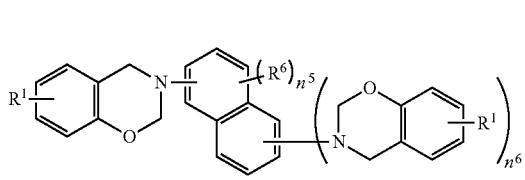
(1-d)

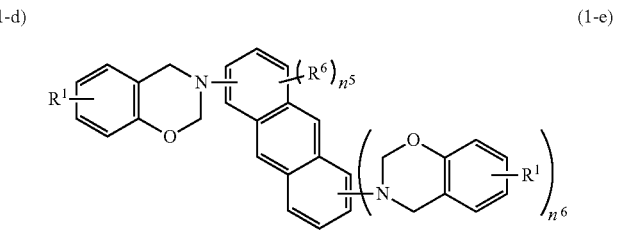
(1-e)

-continued
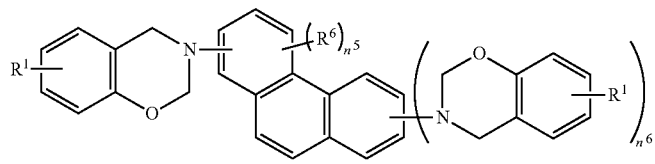
(1-f)
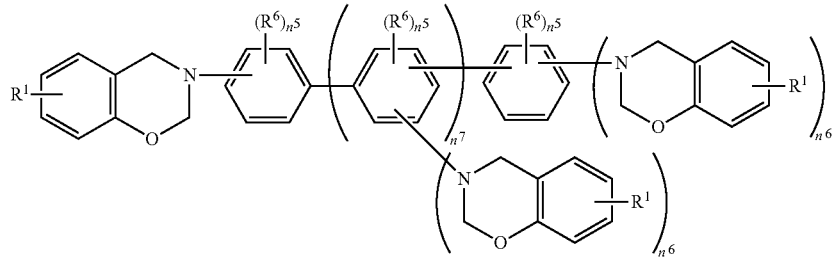
(1-g)
[Chem. 26]
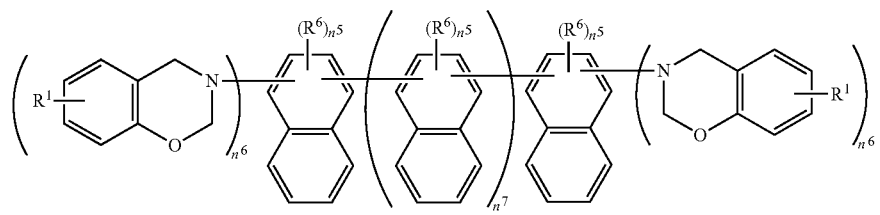
(1-h)
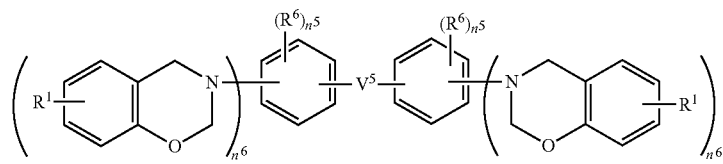
(1-i)
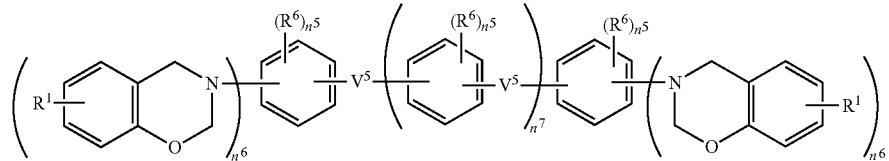
(1-j)
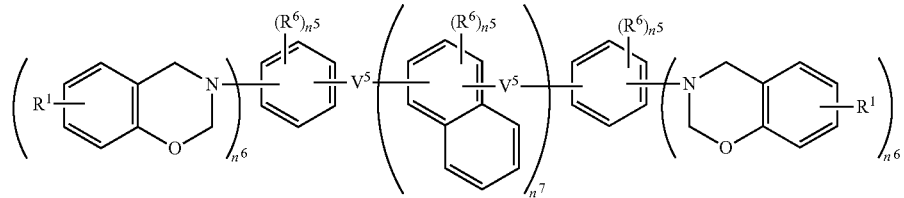
(1-k)
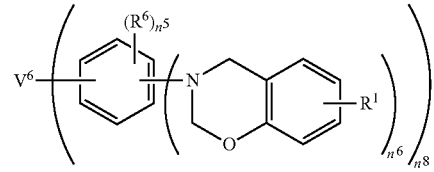
(1-l)

-continued
[Chem. 27]
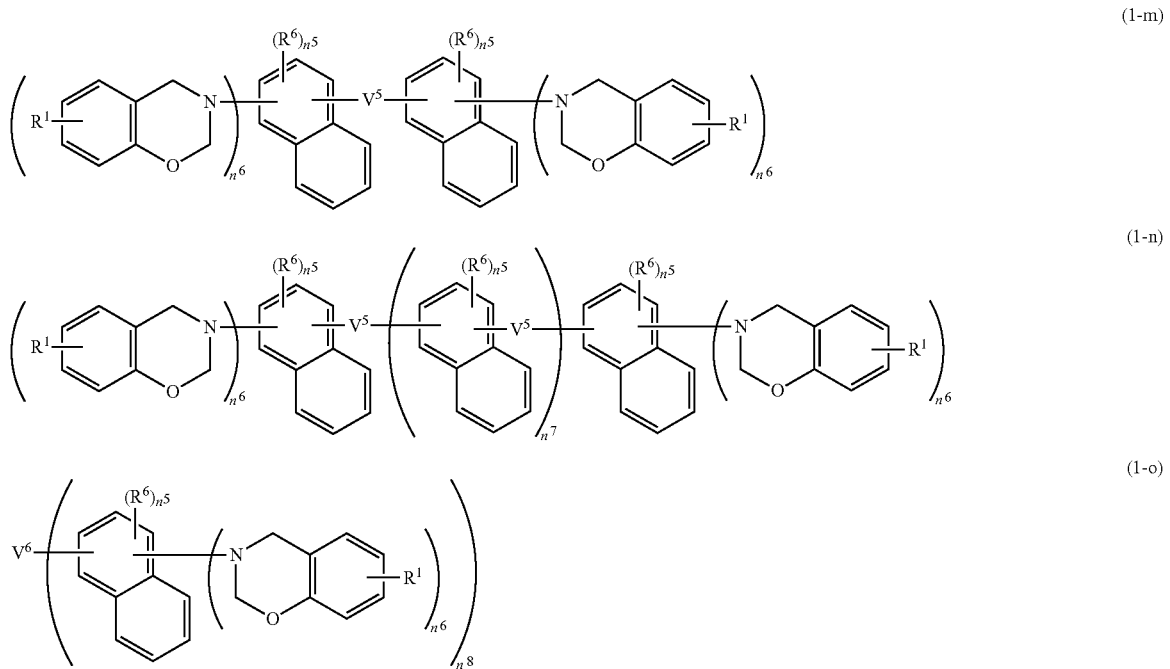
(1-m)
(1-n)
(1-o)
[Chem. 28]
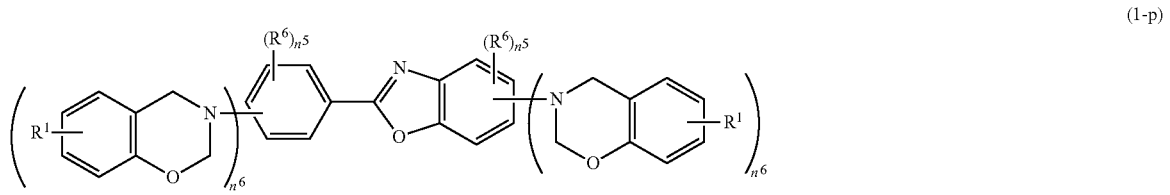
(1-p)
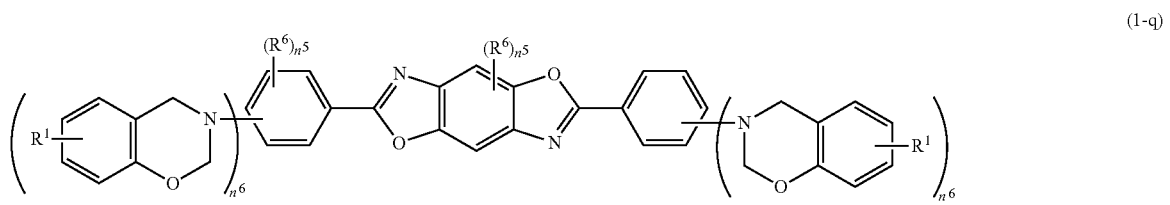
(1-q)
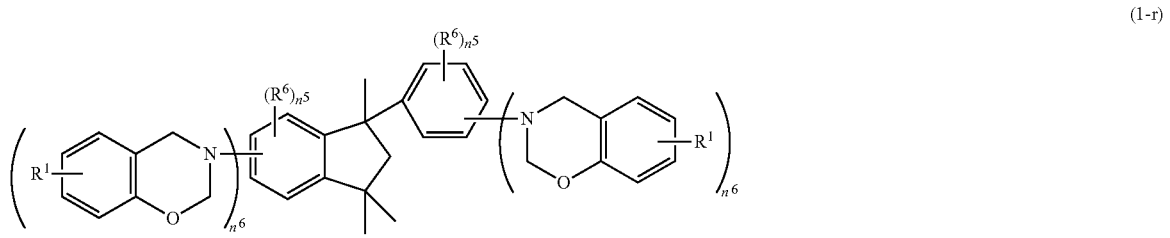
(1-r)

(In Formulae (1-a) and (1-r), $n^5$'s each independently represent an integer of 1 to 4, $n^6$'s each independently represent an integer of 1 to 3, $n^7$'s each independently represent 1 or 2, $n^8$'s each independently represent an integer of 1 to 4, $n^9$'s each independently represent 1 or 2, and $V^5$'s each independently represent a single bond or a divalent linking group, and each independently represent a single bond, a nitrogen atom, an oxygen atom, an alkylene group, an arylene group, a carbonyl group, an ester group, an amide group, an imino group, an azo group, a sulfide group, a sulfone group, or any one of groups obtained by combining two or more of these groups. $V^6$'s each independently represent a linking group having a valence of $n^8+1$, and represent any one of the linking groups selected from Formulae (6-1) to (6 to 7) other than a nitrogen atom, an alkylene group, and an aralkylene group.)

[Chem. 29]

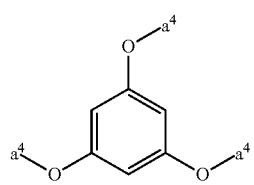

(6-1)

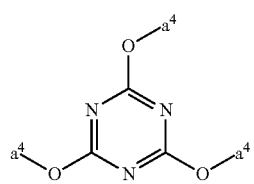

(6-2)

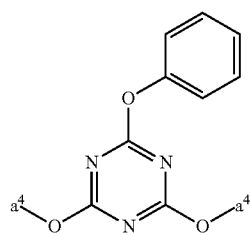

(6-3)

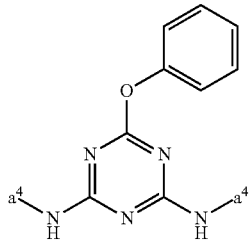

(6-4)

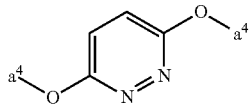

(6-5)

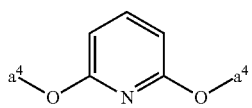

(6-6)

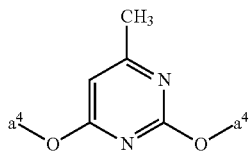

(6-7)

($a^4$ in formulae (6-1) to (6-7) represents the bonding position to the aromatic ring in (1-1) and (1-o).)

$R^6$ is a hydrogen atom, a hydrocarbon group, or a hydrocarbon group in which at least one hydrogen atom contained in the hydrocarbon group is substituted with any one of a hydroxyl group, an alkoxy group, and a halogen atom, in addition to the group represented by $R^1$.

Among them, a particularly preferable structure is a compound represented by Formulae (1-s) and (1-ae).

[Chem. 30]

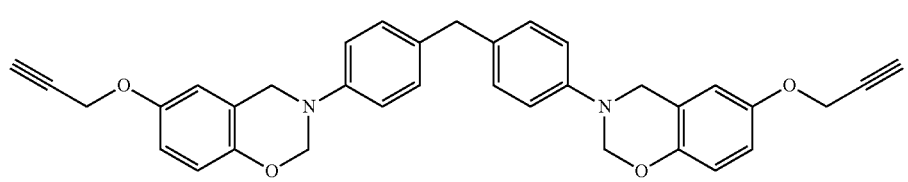

(1-s)

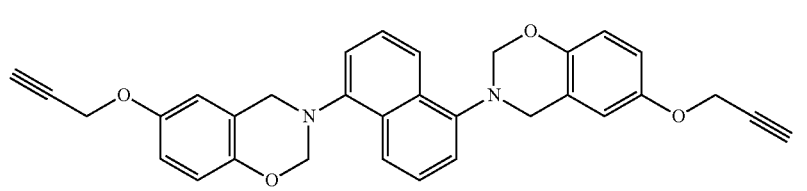

(1-t)

-continued
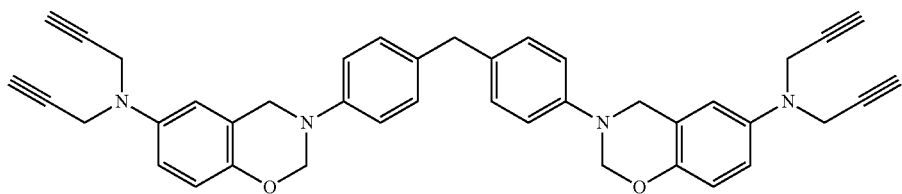
(1-u)
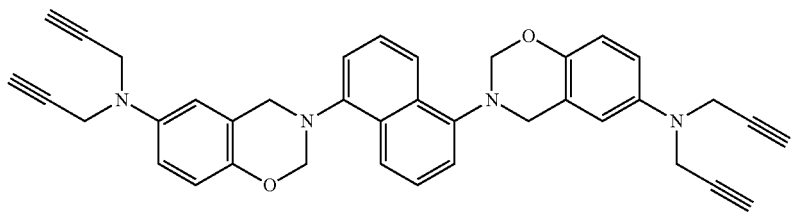
(1-v)
[Chem. 31]
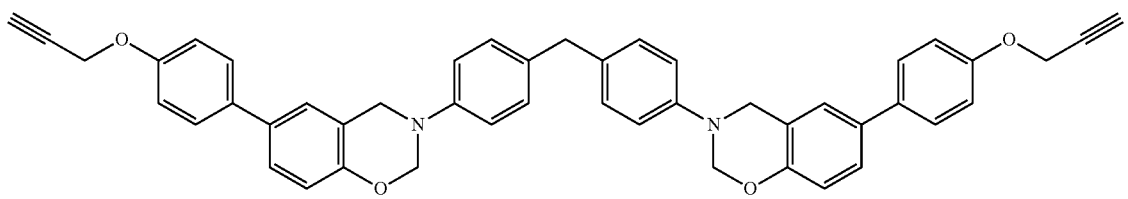
(1-w)
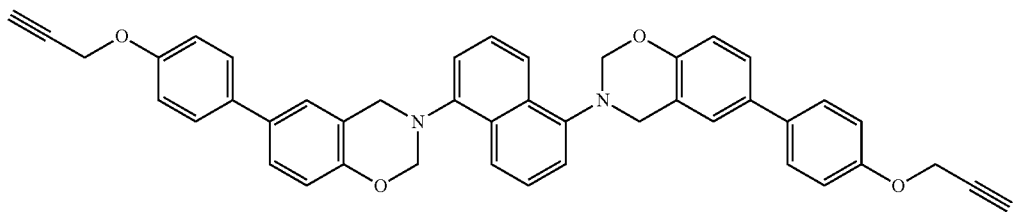
(1-x)
[Chem. 32]
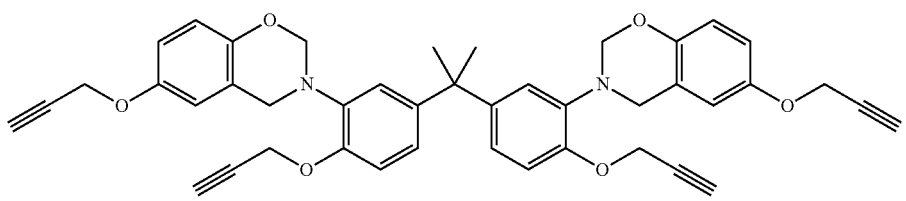
(1-y)
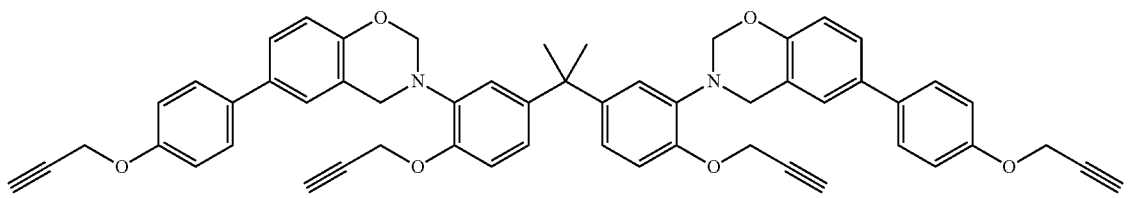
(1-z)
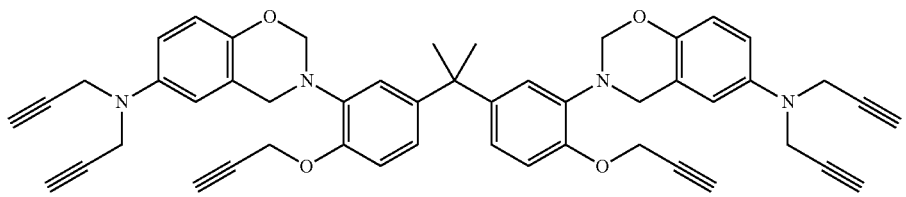
(1-aa)

[Chem. 33]

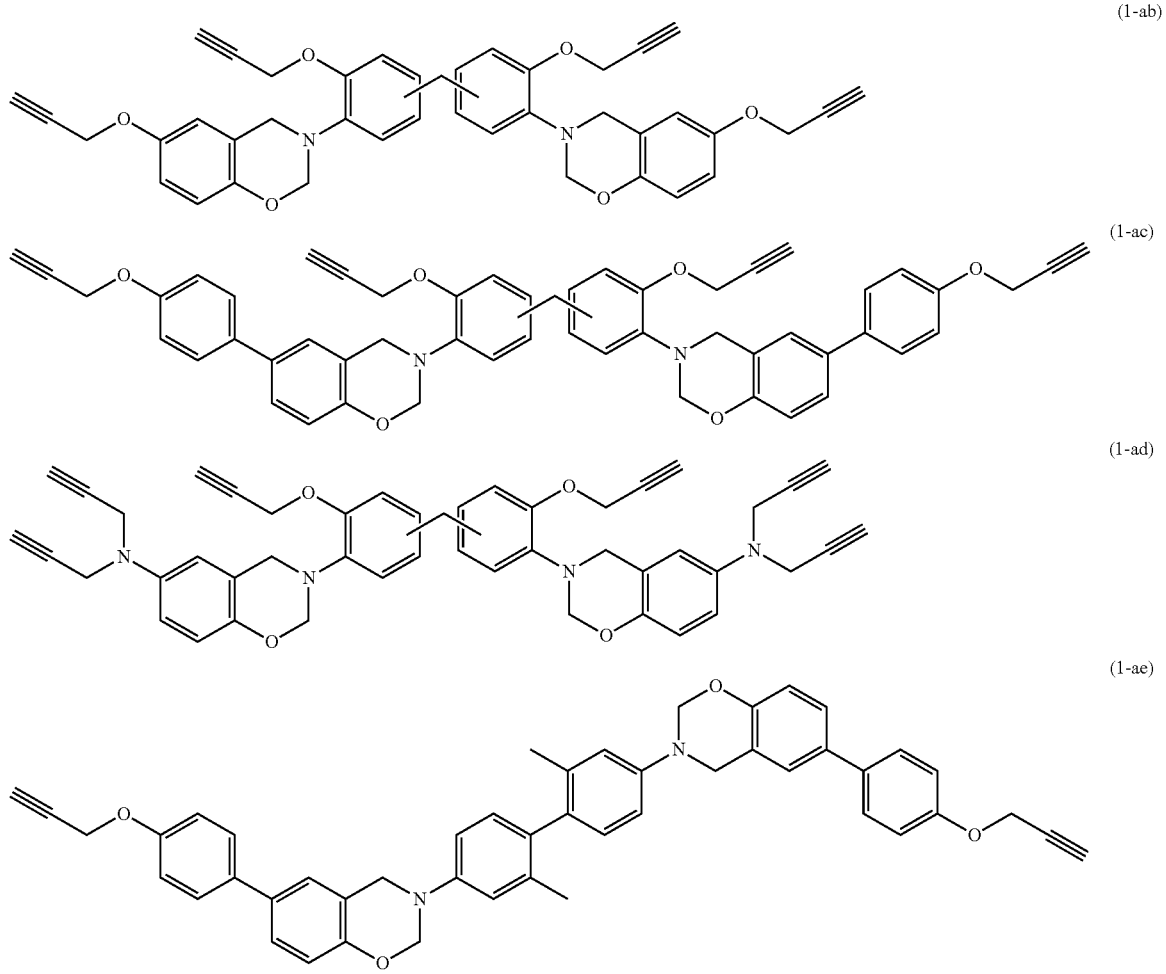

(1-ab)

(1-ac)

(1-ad)

(1-ae)

Among them, a particularly preferable structure is a compound represented by Formulae (1-s), (1-t), (1-z), (1-ac), and (1-ae).

<Method of Preparing Oxazine Compound>

The oxazine compound of the present invention can be obtained by allowing a phenol compound in which a reactive functional group is introduced to a molecular skeleton, and an aromatic amino compound to react with formaldehyde. Examples of the reactive functional group include an ethynyl group, a propargyloxy group, and a N,N-dipropargylamino group. Examples of the phenol compound in which a reactive functional group is introduced to the molecular skeleton is introduced include 2-propargyloxyphenol, 3-propargyloxyphenol, 4-propargyloxyphenol, 3-(N,N-dipropargyl) aminophenol, 4-(N,N-dipropargyl) aminophenol, 4'-propargyloxy-4-biphenol, 4'-propargyloxy-3-biphenol, 4'-propargyloxy-2-biphenol, 2-propargyloxy-1-naphthol, 3-propargyloxy-1-naphthol, 4-propargyloxy-1-naphthol, 5-propargyloxy-1-naphthol, 6-propargyloxy-1-naphthol, 7-propargyloxy-1-naphthol, 8-propargyloxy-1-naphthol, 1-propargyloxy-2-naphthol, 3-propargyloxy-2-naphthol, 6-propargyloxy-2-naphthol, and 7-propargyloxy-2-naphthol. 4,4'-diaminodiphenylmethane, 4,4'-diaminodiphenyl ether, 3,4'-diaminodiphenyl ether, 4,4'-diaminodiphenyl sulfone, ortho-phenylenediamine, Meta-phenylenediamine, p-phenylenediamine, and 1,-diaminonaphthalene can be exemplified. As to the reaction, for example, the phenol compound in which the reactive functional group is introduced to the molecular skeleton, and the aromatic amino compound in which the reactive functional group is introduced to the molecular skeleton react with formaldehyde under the temperature condition of 50° C. to 100° C., the aqueous layer and the organic layer are separated after completion of the reaction, and then an organic solvent is dried under reduced pressure from an organic layer, thereby obtaining an oxazine compound.

In addition, formaldehyde may be used in the form of either formalin which is in a solution state or paraformaldehyde which is in a solid state.

<Resin Composition>

The resin composition of the present invention contains the oxazine compound of the present invention.

The cured product obtained by curing the resin composition of the present invention is excellent in the thermal decomposition resistance, and excellent in the dielectric properties and the low hygroscopicity, and thus can be preferably used for a heat-resistant member and an electronic member.

<Reactive Compound>

The resin composition of the present invention may contain a compound to be blended therein besides the oxazine compound of the present invention.

For example, the resin composition may have a reactive compound other than the oxazine compound of the present invention. The reactive compound referred to here is a compound having a reactive group, which may be a monomer, an oligomer, or a polymer.

The reactive group may be a functional group which does not react with the oxazine compound of the present invention or a functional group which reacts with the oxazine compound, but in order to further improve the heat resistance, the functional group which reacts with the oxazine compound of the present invention is preferable.

Examples of the functional group which reacts with the oxazine compound of the present invention include an epoxy group, a cyanato group, a maleimide group, and a phenolic hydroxyl group.

Examples of the compound having an epoxy group include an epoxy resin and a phenoxy resin.

Examples of the compound having a cyanato group include a cyanate ester resin.

Examples of the compound having a maleimide group include a maleimide resin and a bismaleimide compound. Examples of the compound having a phenolic hydroxyl group include a phenol resin and a phenol compound.

The above-described reactive compound may have only one kind of reactive group, or plural kinds of reactive groups. Also, the number of the functional groups may be one or plural.

Preferable examples of the reactive compound include an epoxy resin, a phenoxy resin, a cyanate ester resin, a maleimide compound, a phenol compound, and an oxazine compound other than the oxazine compound obtained by the present invention.

The epoxy resin is not particularly limited as long as it has an epoxy group, and examples thereof include a bisphenol A type epoxy resin, a bisphenol F type epoxy resin, a bisphenol E type epoxy resin, a bisphenol S type epoxy resin, a bisphenol sulfide type epoxy resin, a phenylene ether type epoxy resin, a naphthylene ether type epoxy resin, a biphenyl type epoxy resin, a tetramethylbiphenyl type epoxy resin, a polyhydroxy naphthalene type epoxy resin, a phenol novolac type epoxy resin, a cresol novolac type epoxy resin, a triphenylol methane type epoxy resin, a tetraphenylolmethane type epoxy resin, a tetraphenylolethane type epoxy resin, a dicyclopentadiene-phenol addition reaction type epoxy resin, a phenol aralkyl type epoxy resin, a naphthol novolac type epoxy resin, a naphthol aralkyl type epoxy resin, a biphenyl aralkyl type epoxy resin, a naphthol-phenol co-condensed novolac type epoxy resin, a naphthol-cresol co-condensed novolac type epoxy resin, a naphthylene ether type epoxy resin, an aromatic hydrocarbon formaldehyde resin modified phenolic resin type epoxy resin, a biphenyl modified novolac type epoxy resin, and an anthracene type epoxy resin. Each of these may be used alone, or two or more kinds thereof may be used in combination.

The phenoxy resin is a high molecular weight thermoplastic polyether resin based on diphenol and epihalohydrin such as epichlorohydrin, and the weight average molecular weight is preferably 20,000 to 100,000. Examples of the structure of the phenoxy resin include structures having one or more kinds selected from a bisphenol A skeleton, a bisphenol F skeleton, a bisphenol S skeleton, a bisphenol acetophenone skeleton, a novolac skeleton, a biphenyl skeleton, a fluorene skeleton, a dicyclopentadiene skeleton, a norbornene skeleton, a naphthalene skeleton, an anthracene skeleton, an adamantane skeleton, a terpene skeleton, and a trimethyl cyclohexane skeleton.

Examples of the cyanate ester resin include a bisphenol A type cyanate ester resin, a bisphenol F type cyanate ester resin, a bisphenol E type cyanate ester resin, a bisphenol S type cyanate ester resin, a bisphenol sulfide type cyanate ester resin, a phenylene ether type cyanate ester resin, a naphthylene ether type cyanate ester resin, a biphenyl type cyanate ester resin, a tetramethylbiphenyl type cyanate ester resin, a polyhydroxy naphthalene type cyanate ester resin, a phenol novolac type cyanate ester resin, a cresol novolac type cyanate ester resin, a triphenylmethane type cyanate ester resin, a tetraphenylethane type cyanate ester resin, a dicyclopentadiene-phenol addition reaction type cyanate ester resin, a phenol aralkyl type cyanate ester resin, a naphthol novolac type cyanate ester resin, a naphthol aralkyl type cyanate ester resin, a naphthol-phenol co-condensed novolac type cyanate ester resin, a naphthol-cresol co-condensed novolac type cyanate ester resin, an aromatic hydrocarbon formaldehyde resin-modified phenol resin type cyanate ester resin, a biphenyl modified novolac type cyanate ester resin, and an anthracene type cyanate ester resin. Each of these may be used alone, or two or more kinds thereof may be used in combination.

Among these cyanate ester resins, in particular, from the viewpoint of obtaining a cured product excellent in the heat resistance, a bisphenol A type cyanate ester resin, a bisphenol F type cyanate ester resin, a bisphenol E type cyanate ester resin, a polyhydroxy naphthalene type cyanate ester resin, a naphthylene ether type cyanate ester resin, and a novolac type cyanate ester resin are preferable, and from the viewpoint of obtaining a cured product excellent in dielectric properties, a dicyclopentadiene-phenol addition reaction type cyanate ester resin is preferable.

As the maleimide compound, for example, various compounds represented by any one of Structural Formulae (i) to (iii) can be exemplified.

[Chem. 34]

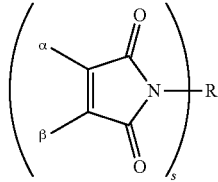

(i)

(In the formula, R is an m-valent organic group, α and β are each a hydrogen atom, a halogen atom, an alkyl group, or an aryl group, and s is an integer of 1 or more.)

[Chem. 35]

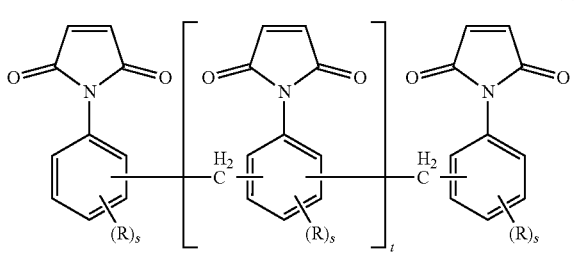

(ii)

(In the formula, R is any one of a hydrogen atom, an alkyl group, an aryl group, an aralkyl group, a halogen atom, a hydroxyl group, and an alkoxy group, s is an integer of 1 to 3, and t is an average of 0 to 10 on a repeating unit.)

[Chem. 36]

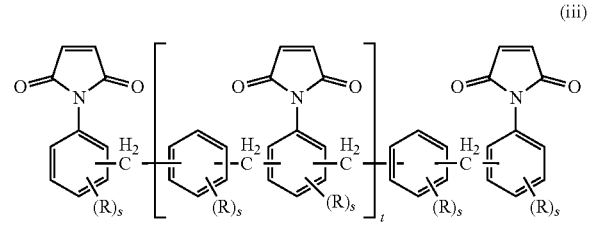

(iii)

(In the formula, R is any one of a hydrogen atom, an alkyl group, an aryl group, an aralkyl group, a halogen atom, a hydroxyl group, and an alkoxy group, s is an integer of 1 to 3, and t is an average of 0 to 10 on a repeating unit.)

Each of these compounds may be used alone, or two or more kinds thereof may be used in combination.

The phenolic hydroxyl group-containing compound is not particularly limited as long as it has a phenolic hydroxyl group, and examples thereof include bisphenol A, bisphenol F, bisphenol E, bisphenol S, bisphenol sulfide, dihydroxydiphenyl ether, a hydroxypolyphenylene ether compound, a hydroxynaphthylene ether compound, biphenol, tetramethylbiphenol, terphenyl diol, polyhydroxy naphthalene, a phenol novolac resin, a cresol novolac resin, triphenylol methane, tetraphenylolmethane, tetraphenylolethane, a dicyclopentadiene-phenol addition reaction product, a phenol aralkyl compound, a hydroxybiphenyl aralkyl compound, a naphthol novolac compound, a naphthol aralkyl compound, a naphthol-phenol co-condensed novolac resin, a naphthol-cresol co-condensed novolac resin, an aromatic hydrocarbon formaldehyde resin-modified phenol compound, a biphenyl modified phenolic resin (a polyhydric phenol compound in which a phenol nucleus is linked with a bismethylene group), a biphenyl modified naphthol resin (a polyhydric naphthol compound in which a phenol nucleus is linked with a bismethylene group), an aminotriazine-modified phenolic resin (a polyhydric phenol compound in which a phenol nucleus is linked with melamine, benzoguanamine, and the like), and a polyhydric phenol compound such as an alkoxy group-containing aromatic ring-modified novolac resin (a polyhydric phenol compound in which a phenol nucleus and an alkoxy group-containing aromatic ring are linked with formaldehyde), and hydroxyanthracene. Each of these may be used alone, or two or more kinds thereof may be used in combination.

The oxazine compound other than the oxazine compound obtained by the present invention is not particularly limited, and examples thereof include a reaction product of bisphenol F, formalin, and aniline (a F-a type benzoxazine resin), a reaction product of 4,4'-diaminodiphenylmethane, formalin, and phenol (a P-d type benzoxazine resin), a reaction product of bisphenol A, formalin, and aniline, a reaction product of dihydroxydiphenyl ether, formalin, and aniline, a reaction product of diaminodiphenyl ether, formalin, and phenol, a reaction product of dicyclopentadiene-phenol addition type resin and formalin, and aniline, a reaction product of phenolphthalein, formalin, and aniline, and a reaction product of dihydroxydiphenyl sulfide, formalin, and aniline. Each of these may be used alone, or two or more kinds thereof may be used in combination.

<Filler>

The composition of the present invention may further contain a filler in addition to the oxazine compound. Examples of the filler include an inorganic filler and an organic filler. Examples of the inorganic filler include an inorganic fine particle.

Examples of the inorganic fine particle include alumina, magnesia, titania, zirconia, silica (quartz, fumed silica, precipitated silica, silicic anhydride, fused silica, crystalline silica, ultrafine amorphous silica, and the like), and the like as a material having excellent heat resistance; boron nitride, aluminum nitride, alumina oxide, titanium oxide, magnesium oxide, zinc oxide, silicon oxide, and the like as a material having excellent thermal conductivity; a metal filler and/or a metal-coated filler using a metal simple substance or an alloy (for example, iron, copper, magnesium, aluminum, gold, silver, platinum, zinc, manganese, and stainless steel) as a material having excellent conductivity; minerals such as mica, clay, kaolin, talc, zeolite, wollastonite, and smectite, and potassium titanate, magnesium sulfate, sepiolite, zonolite, aluminum borate, calcium carbonate, titanium oxide, barium sulfate, zinc oxide, and magnesium hydroxide as a material having excellent barrier properties; barium titanate, zirconia oxide, titanium oxide, and the like as a material having a high refractive index; photocatalytic metals such as titanium, cerium, zinc, copper, aluminum, tin, indium, phosphorus, carbon, sulfur, terium, nickel, iron, cobalt, silver, molybdenum, strontium, chromium, barium, and lead, a composite of the metal, oxides thereof, and the like as a material exhibiting photocatalytic properties; metals such as silica, alumina, zirconia, and magnesium oxide, complexes and oxides thereof, and the like as a material having excellent abrasion resistance; metals such as silver and copper, tin oxide, indium oxide, and the like as a material having excellent conductivity; and silica and the like as a material having excellent insulating properties; and titanium oxide, zinc oxide, and the like as a material having excellent ultraviolet shielding.

These inorganic fine particles may be appropriately selected depending on the application, and may be used alone or plural kinds thereof may be used in combination. In addition, the inorganic fine particles have various features besides the features exemplified in the examples, and thus may be selected according to the application as required.

For example, in the case where silica is used as an inorganic fine particle, there is no particular limitation, and known silica fine particles such as powdered silica and colloidal silica can be used. Examples of commercially available powdered silica fine particles include Aerosil 50,200 manufactured by Nippon Aerosil Co., Ltd., SILDEX H31, H32, H51, H52, H121, and H122 manufactured by Asahi Glass Co., Ltd., E220A and E220 manufactured by Nippon Silica Industry Co., SYLYSIA 470 Fuji Silysia chemical Co., Ltd., and SG Flake manufactured by Nippon Sheet Glass Co., Ltd.

Examples of commercially available colloidal silica include methanol silica sol, IPA-ST, MEK-ST, NBA-ST, XBA-ST, DMAC-ST, ST-UP, ST-OUP, ST-20, ST-40, ST-C, ST-N, ST-O, ST-50, and ST-OL manufactured by Nissan Chemical Industries, Ltd.

Surface-modified silica fine particles may be used, and examples thereof include those obtained by surface-treating the silica fine particles with a reactive silane coupling agent having a hydrophobic group or those modified with a compound having a (meth)acryloyl group. Examples of the commercially available powdered silica modified with a compound having a (meth)acryloyl group include Aerosil RM50 and R711 manufactured by Nippon Aerosil Co., Ltd., and examples of the commercially available colloidal silica modified with a compound having a (meth)acryloyl group include MIBK-SD manufactured by Nissan Chemical Industries, Ltd.

The shape of the silica fine particle is not particularly limited, and spherical, hollow, porous, rod, plate, fiber, or irregular shapes can be used. The primary particle size is preferably in the range of 5 to 200 nm. If it is smaller than 5 nm, the inorganic fine particle in the dispersion is not sufficiently dispersed, and if it is larger than 200 nm, sufficient strength of the cured product may not be maintained.

As the titanium oxide fine particle, not only an extender pigment but also an ultraviolet photoresponsive photocatalyst can be used. For example, anatase type titanium oxide, rutile type titanium oxide, and brookite type titanium oxide can be used. It is also possible to use particles designed to cause the crystal structure of titanium oxide to be doped with different elements so as to respond to visible light. An anion element such as nitrogen, sulfur, carbon, fluorine, and phosphorus, or a cationic element such as chromium, iron, cobalt, and manganese is suitably used as an element to be doped in titanium oxide. In addition, as a form, a sol or slurry dispersed in powder, organic solvent, or water can be used. Examples of commercially available powdered titanium oxide fine particles include Aerosil P-25 manufactured by Nippon Aerosil Co., Ltd., and ATM-100 manufactured by Tayca Corporation. Examples of commercially available slurry-like fine titanium oxide particles include TKD-701 manufactured by Tayca Corporation.

<Fibrous Substrate>

The composition of the present invention may further contain a fibrous substrate in addition to the oxazine compound. The fibrous substrate of the present invention is not particularly limited, and is preferably those used for a fiber-reinforced resin, and examples thereof include inorganic fiber or organic fiber.

As the inorganic fiber, in addition to inorganic fibers such as carbon fiber, glass fiber, boron fiber, alumina fiber, and silicon carbide fiber, mineral fibers such as carbon fiber, activated carbon fiber, graphite fiber, glass fiber, tungsten carbide fiber, silicon carbide fiber (silicon carbide fiber), ceramic fiber, alumina fiber, natural fiber, and basalt, and boron fiber, boron nitride fiber, boron carbide fiber, metal fiber, and the like can be exemplified. Examples of the metal fibers include aluminum fiber, copper fiber, brass fiber, stainless steel fiber, and steel fiber.

As the organic fiber, synthetic fibers made of a resin material such as polybenzazole, aramid, PBO (polyparaphenylene benzoxazole), polyphenylene sulfide, polyester, acrylic, polyamide, polyolefin, polyvinyl alcohol, and polyarylate; natural fibers such as cellulose, pulp, cotton, wool, and silk, and regenerated fibers such as proteins, polypeptides, and alginic acid can be exemplified.

Among them, carbon fiber and glass fiber have wide industrial applicability, and thus preferably used. Among them, only one kind may be used, or plural kinds may be used at the same time.

The fibrous substrate of the present invention may be an aggregate of fibers, and the fibers may be continuous or discontinuous, and may be woven cloth or nonwoven cloth. In addition, fiber bundles in which fibers are aligned in one direction may be used, or a sheet form in which fiber bundles are arranged may be used. Further, a three-dimensional form of aggregate of fibers having a thickness may be used.

<Dispersion Medium>

In the composition of the present invention, a dispersion medium may be used for the purpose of adjusting the solid content and viscosity of the composition. As the dispersion medium, any liquid medium may be used as long as the effect of the present invention is not impaired, and various organic solvents, liquid organic polymers, and the like can be exemplified.

Examples of the organic solvent include ketones such as acetone, methyl ethyl ketone (MEK), and methyl isobutyl ketone (MIBK), cyclic ethers such as tetrahydrofuran (THF) and dioxolane, esters such as methyl acetate, ethyl acetate, and butyl acetate, aromatic compounds such as toluene and xylene, and alcohols such as carbitol, cellosolve, methanol, isopropanol, butanol, and propylene glycol monomethyl ether. These can be used alone or in combination, and among them, methyl ethyl ketone is preferable from the viewpoint of volatility at the time of coating and solvent recovery.

The liquid organic polymer is a liquid organic polymer that does not directly contribute to the curing reaction, and examples thereof include a carboxyl group-containing polymer modified product (Floren G-900, NC-500: Kyoeisha Co., LTD.), acrylic polymers (Floren WK-20: Kyoeisha Co., LTD.), an amine salt of a special modified phosphate ester (HIPLAAD ED-251: Kusumoto Chemicals, Ltd.), and a modified acrylic block copolymer (DISPERBYK 2000; BYK Additives & Instruments).

<Resin>

In addition, the composition of the present invention may have a resin other than the oxazine compound. As the resin, a known and commonly used resin may be blended as long as the effect of the present invention is not impaired, and examples thereof include a thermosetting resin or a thermoplastic resin.

The thermosetting resin is a resin having the property of changing to be substantially insoluble and infusible when being cured by heating or by means such as radiation or catalyst. Specific examples thereof include a phenol resin, a urea resin, a melamine resin, a benzoguanamine resin, an alkyd resin, an unsaturated polyester resin, a vinyl ester resin, a diallyl terephthalate resin, an epoxy resin, a silicone resin, a urethane resin, a furan resin, a ketone resin, a xylene resin, a thermosetting polyimide resin, and a benzoxazine resin other than the oxazine compound obtained by the present invention. These thermosetting resins can be used alone or two or more kinds thereof may be used in combination.

The thermoplastic resin is a resin which can be melt-molded through heating. Specific examples thereof include a polyethylene resin, a polypropylene resin, a polystyrene resin, a rubber modified polystyrene resin, an acrylonitrile-butadiene-styrene (ABS) resin, an acrylonitrile-styrene (AS) resin, a polymethyl methacrylate resin, an acrylic resin, a polyvinyl chloride resin, a polyvinylidene chloride resin, a polyethylene terephthalate resin, an ethylene vinyl alcohol resin, a cellulose acetate resin, a ionomer resin, a polyacrylonitrile resin, a polyamide resin, a polyacetal resin, a polybutylene terephthalate resin, a polylactic acid resin, a polyphenylene ether resin, a modified polyphenylene ether resin, a polycarbonate resin, a polysulfone resin, a polyphenylene sulfide resin, a polyetherimide resin, a polyethersulfone resin, a polyarylate resin, a thermoplastic polyimide resin, a polyamide imide resin, a polyetheretherketone resin, a polyketone resin, a liquid crystal polyester resin, a fluorine resin, a syndiotactic polystyrene resin, and a cyclic polyolefin resin. These thermoplastic resins can be used alone or two or more kinds thereof may be used in combination.

<Curing Agent>

In the composition of the present invention, a curing agent may be used depending on the compound blended therein, for example, in the case where a compound having an epoxy group is blended, various kinds of curing agents such as an amine-based curing agent, an amide-based curing agent, an acid anhydride-based curing agent, a phenol-based curing agent, an aminotriazine novolac resin, an active ester resin, and a resin having a functional group capable of reacting with an epoxy group, such as carboxyl group or thiol, may be used in combination.

Examples of the amine-based curing agent include diaminodiphenyl methane, diaminodiphenyl ether, diaminodiphenyl ether, diaminodiphenyl sulfone, orthophenylene diamine, meta-phenylene diamine, paraphenylene diamine, metaxylene diamine, paraxylene diamine, diethyl toluene diamine, diethylene triamine, triethylene tetramine, isophorone diamine, imidazole, a BF3-amine complex, a guanidine derivative, and a guanamine derivative.

Examples of the amide-based curing agent include dicyandiamide, a polyamide resin synthesized from a dimer of linolenic acid and ethylenediamine.

Examples of the acid anhydride-based curing agent include phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, and methyl hexahydrophthalic anhydride.

Examples of the phenolic curing agent include bisphenol A, bisphenol F, bisphenol S, resorcin, catechol, hydroquinone, fluorene bisphenol, 4,4'-biphenol, 4,4',4"-trihydroxytriphenylmethane, naphthalene diol, 1,1,2,2-tetrakis (4-hydroxyphenyl) ethane, calixarene, a phenol novolac resin, a cresol novolac resin, an aromatic hydrocarbon formaldehyde resin-modified phenolic resin, a dicyclopentadiene phenol addition type resin, a phenol aralkyl resin (a xyloc resin), a polyhydric phenol novolac resin synthesized from a polyhydric hydroxy compound typified by a resorcin novolac resin and formaldehyde, a naphthol aralkyl resin, a trimethylolmethane resin, a tetraphenylolethane resin, a naphthol novolac resin, a naphthol-phenol co-condensed novolac resin, a naphthol-cresol co-condensed novolac resin, and polyhydric phenol compounds such as a biphenyl modified phenolic resin (a polyhydric phenol compound in which a phenol nucleus is linked with a bismethylene group), a biphenyl modified naphthol resin (a polyhydric phenol compound in which a phenol nucleus is linked with a bismethylene group), an aminotriazine-modified phenol resin (a polyhydric phenol compound in which a phenol nucleus is linked with melamine, benzoguanamine, or the like), and an alkoxy group-containing aromatic ring-modified novolac resin (a polyhydric phenol compound in which a phenol nucleus and an alkoxy group-containing aromatic ring are linked with formaldehyde).

These curing agents may be used alone or two or more kinds thereof may be used in combination.

In addition, in the case where the composition of the present invention contains the compound having an epoxy group, a cure accelerator may be used alone or may be used in combination with the curing agent. Various compounds which accelerate the curing reaction of the epoxy resin may be used as the cure accelerator, and examples thereof include a phosphorus compound, a tertiary amine compound, an imidazole compound, an organic acid metal salt, a Lewis acid, and an amine complex salt. Among them, an imidazole compound, a phosphorus compound, or a tertiary amine compound is preferably used, and particularly in the case being used for a semiconductor sealing material application, triphenylphosphine for the phosphorus compound and 1,8-diazabicyclo-[5.4.0]-undecene (DBU) for the tertiary amine are preferably used from the viewpoint of excellent curability, heat resistance, electrical characteristics, moisture resistance reliability, and the like.

<Other Compounds>

The composition of the present invention may contain other compounds to be blended. Examples of the other compounds include a catalyst, a polymerization initiator, an inorganic pigment, an organic pigment, an extender pigment, clay mineral, wax, a surfactant, a stabilizer, a flow regulator, a coupling agent, dye, a leveling agent, a rheology control agent, a UV absorber, an antioxidant, a flame retardant, and a plasticizer.

<Cured Product>

The cured product obtained by curing the composition of the present invention is excellent in the thermal decomposition resistance, and the dielectric properties, and the low hygroscopicity, and thus can be preferably used for a heat-resistant member and an electronic member. A method of molding a cured product is not particularly limited, and the composition may be molded alone, or may be molded as a laminate by laminating with a base material.

In the case of curing the composition of the present invention, thermal curing may be performed. Known conventional curing catalysts may be used during the thermal curing, but the composition of the present invention can be cured without using a curing agent by the reaction between the oxazine skeleton and carbon-carbon triple bond.

In the case of using the curing catalyst, examples thereof include inorganic acids such as hydrochloric acid, sulfuric acid, phosphoric acid and the like; organic acids such as p-toluenesulfonic acid, monoisopropyl phosphate and acetic acid; inorganic bases such as sodium hydroxide or potassium hydroxide; titanate esters such as tetraisopropyl titanate and tetrabutyl titanate; compounds containing various basic nitrogen atoms such as 1,8-diazabicyclo [5.4.0] undecene-7 (DBU), 1,5-diazabicyclo [4.3.0] nonene-5 (DBN), 1,4-diazabicyclo [2.2.2] octane (DABCO), tri-n-butylamine, dimethyl benzylamine, monoethanolamine, imidazole, and 1-methyl imidazole; various quaternary ammonium salts such as tetramethyl ammonium salt, tetrabutyl ammonium salt, and dilauryldimethyl ammonium salt; as a counter anion, quaternary ammonium salts having chloride, bromide, carboxylate, or hydroxide; tin carboxylates such as dibutyltin diacetate, dibutyltin dioctoate, dibutyltin dilaurate, dibutyltin diacetylacetonate, tin octylate, or stearate. The catalysts may be used alone or two or more kinds thereof may be used in combination.

As the base material of the laminate, an inorganic material such as metal or glass, an organic material such as plastic or wood, and the like may be suitably used depending on the application, and the shape of the laminate may be a flat plate, or a sheet shape, or the laminate may have a three-dimensional structure or may have a three-dimensional shape. The laminate may have any shape according to the purpose, such as one having curvature on the whole surface or a part thereof. Also, the hardness, thickness, and the like of the base material are not limited. In addition, the cured product of the present invention may be set as a base material, and the cured product of the present invention may be further laminated.

In applications for a circuit board and a semiconductor package substrate, it is preferable to laminate a metal foil, and examples of the metal foil include a copper foil, an aluminum foil, a gold foil, and a silver foil, and from the viewpoint of good workability, a copper foil is preferably used.

In the laminate of the present invention, a layer of the cured product may be formed directly on the base material by coating or molding, and those already molded may be laminated. In the case of direct coating, the coating method is not particularly limited, and examples thereof include a spray method, a spin coating method, a dipping method, a roll coating method, a blade coating method, a doctor roll method, a doctor blade method, a curtain coating method, a slit coating method, a screen printing method, and an ink jet method. In the case of direct molding, in-mold molding, insert molding, vacuum molding, extrusion lamination molding, press molding and the like can be exemplified.

In the case of laminating the composition subjected to molding, the uncured or semi-cured composition layer may be laminated and then cured, or the layer of the cured product in which the composition is completely cured may be laminated on the base material.

In addition, the cured product of the present invention may be laminated by applying and curing a precursor which can serve as a base material, and the precursor which can serve as a base material or the composition of the present invention being bonded in an uncured or semi-cured state may be bonded and then cured. The precursor which can serve as a base material is not particularly limited, and various kinds of curable resin compositions can be exemplified.

<Fiber-Reinforced Resin>

In the case where the composition of the present invention contains a fibrous substrate which is a reinforced fiber, the composition containing the fibrous substrate can be used as a fiber-reinforced resin.

The method of incorporating the fibrous substrate in the composition is not particularly limited as long as it does not impair the effect of the present invention and the fibrous substrate and the composition may be composited by methods such as kneading, applying, impregnating, injecting, and pressing. The method can be suitably selected according to the form of the fiber and the use of the fiber-reinforced resin.

The method of molding the fiber-reinforced resin of the present invention is not particularly limited. If a plate-shaped product is to be produced, an extrusion molding method is generally used, but it is also possible with a flat press. In addition, an extrusion molding method, a blow molding method, a compression molding method, a vacuum molding method, an injection molding method, and the like can be used. When a film-shaped product is to be produced, a solution casting method can be used in addition to a melt extrusion method, and when a melt molding method is used, it is possible to use inflation film molding, cast molding, extrusion lamination molding, calendar molding, sheet molding, fiber molding, blow molding, injection molding, rotational molding, and coating molding. In the case of a resin that is cured by active energy rays, a cured product can be produced using various curing methods using active energy rays. In particular, in the case where a thermosetting resin is used as a main component for a matrix resin, a molding method in which the molding material is made into a prepreg and then pressurized and heated by a press or an autoclave, can be exemplified, and additionally, resin transfer molding (RTM), vaccum assist resin transfer molding (VaRTM), laminate molding, hand lay-up molding, and the like can be exemplified.

<Prepreg>

The fiber-reinforced resin of the present invention can form a state called uncured or semi-cured prepreg. After the product is circulated in the state of the prepreg, the cured product may be formed by final curing. In the case of forming a laminate, the prepreg is formed, the other layers are then laminated thereon, and curing is performed finally, thereby advantageously providing a laminate where each layer is in intimate contact with each other.

Although the mass ratio of the composition and the fibrous substrate used at this time is not particularly limited, it is generally preferable to prepare such that the resin content in the prepreg is 20% to 60% by mass.

<Heat-Resistant Material and Electronic Material>

The cured product utilizing the oxazine compound of the present invention is excellent in the thermal decomposition resistance, the dielectric properties, and the low hygroscopicity, and thus it can be suitably used for a heat-resistant member and an electronic member. In particular, it can be suitably used for a semiconductor sealing material, a circuit board, a build-up film, a build-up substrate, and the like. It can also be suitably used for a matrix resin of a fiber-reinforced resin, and is particularly suitable as a prepreg with high heat resistance. The heat-resistant member and the electronic member thus obtained can be suitably used for various applications, and examples of the various applications include industrial machine parts, general mechanical parts, parts such as automobiles, railway, or vehicles, parts related to space and aviation, electronic and electric parts, building materials, containers and packaging members, daily necessities, sports and leisure goods, and cabin member for wind power generation, but it is not limited to these applications.

Representative products will be described below with examples.

1. Semiconductor Sealing Material

As a method of obtaining a semiconductor sealing material from the composition of the present invention, a method of sufficiently melting and mixing the above composition, a cure accelerator, and a compounding agent such as an inorganic filler using an extruder, a kneader, a roll or the like if necessary, can be exemplified. At this time, fused silica is generally used as the inorganic filler, but when it is used as a high thermal conductive semiconductor sealing material for a power transistor and a power IC, it is preferable to use a high packing density of crystalline silica, alumina, and silicon nitride each having higher thermal conductivity than fused silica, or use fused silica, crystalline silica, alumina, silicon nitride or the like. The filling rate is preferably 30% to 95% by mass of the inorganic filler per 100 parts by mass of the curable resin composition, among them, in order to achieve improvement of flame retardancy, moisture resistance, and solder crack resistance, and decrease in a linear expansion coefficient, it is more preferably equal to or more than 70 parts by mass, and is still more preferably equal to or more than 80 parts by mass.

2. Semiconductor Device

Examples of a semiconductor package molding for obtaining a semiconductor device from the curable resin composition of the present invention include a method in which the semiconductor sealing material is molded using a casting machine, a transfer molding machine, an injection molding machine or the like, and further heated at 50° C. to 250° C. for 2 to 10 hours.

3. Printed Circuit Board

Examples of a method of obtaining a printed circuit board from the composition of the present invention include a method of laminating the above prepregs in a conventional manner, and appropriately laminating a copper foil, and heating and crimping the laminate at 170° C. to 300° C. under pressure of 1 to 10 MPa for 10 minutes to 3 hours.

4. Build-Up Substrate

As a method of obtaining a build-up substrate from the composition of the present invention, for example, the following steps can be exemplified. First, a step in which a circuit substrate on which a circuit is formed is coated with the composition appropriately containing a rubber, a filler, and the like blended therein by using a spray coating method, a curtain coating method, or the like, and then the coated circuit board is cured (step 1). Thereafter, a step in which a hole such as a predetermined through hole portion is drilled, if necessary, then a surface is treated with a roughening agent, the surface is subjected to hot water washing so as to form irregularities, and a plating treatment with metal such as copper is performed (step 2). A step in which such operations are sequentially repeated as desired, and the resin insulating layer and the conductor layers of the predetermined circuit pattern are alternately built up (step 3). Note that, the drilling of the through hole portion is performed after forming the outermost resin insulating layer. Further, in the build-up substrate of the present invention, a resin-coated copper foil obtained by semi-curing the resin composition on a copper foil is heated and pressed onto a circuit board on which a circuit is formed at 170° C. to 300° C., thereby enabling the formation of a build-up substrate while omitting a step of forming a roughened surface and a plating treatment.

5. Build-Up Film

As a method of obtaining a build-up film from the composition of the present invention, a method of producing a layer (X) of the composition formed by coating the surface of a support film (Y) as a base material with the composition and further drying the organic solvent by heating, hot air blowing or the like can be exemplified.

Examples of the organic solvent used here include ketones such as acetone, methyl ethyl ketone, and cyclohexanone, acetate esters such as ethyl acetate, butyl acetate, cellosolve acetate, propylene glycol monomethyl ether acetate, and carbitol acetate, carbitols such as cellosolve and butyl carbitol, aromatic hydrocarbons such as toluene and xylene, dimethyl formamide, dimethyl acetamide, and N-methyl pyrrolidone are preferably used, and, it is preferable to use it in a proportion that the nonvolatile content is 30% to 60% by mass.

The thickness of the layer (X) to be formed is generally equal to or larger than the thickness of the conductor layer. The thickness of the conductor layer of the circuit board is generally 5 to 70 μm, and thus the thickness of the resin composition layer is preferably 10 to 100 μm. The layer (X) of the composition in the present invention may be protected with a protective film described later. Protection with a protective film makes it possible to prevent adhesion of dust or scratches and the like to the surface of the resin composition layer.

Examples of the support film and the protective film include polyolefins such as polyethylene, polypropylene, and polyvinyl chloride, polyethylene terephthalate (hereinafter, abbreviated as "PET" in some cases), polyester such as polyethylene naphthalate, polycarbonate, and polyimide, release paper, and metal foil such as copper foil and aluminum foil. In addition to the mud treatment and the corona treatment, the support film and the protective film may be subjected to a release treatment. The thickness of the support film is not particularly limited, and is generally 10 to 150 μm, and is preferably 25 to 50 μm. The thickness of the protective film is preferably 1 to 40 μm.

The support film (Y) is peeled off after being laminated on a circuit board or after forming an insulating layer by heat curing. Since the support film (Y) is peeled off after the curable resin composition layer constituting the build-up film is cured by heating, adhesion of dust and the like in the curing step can be prevented. In the case of peeling after curing, the support film is generally subjected to the releasing treatment in advance.

A multilayer printed circuit board can be produced using the build-up film obtained as described above. For example, in the case where the layer (X) is protected with a protective film, after separating it therefrom, the layer (X) is laminated on one side or both sides of the circuit board, for example, by a vacuum lamination method, such that the layer (X) is in direct contact with the circuit board. The method of lamination may be batch type or continuous type with roll. If necessary, the build-up film and the circuit board may be heated (pre-heated) before laminating. As to the conditions of the lamination, a crimping temperature (lamination temperature) is preferably 70° C. to 140° C., a crimping pressure is preferably 1 to 11 kgf/cm$^2$ (9.8×104 to 107.9×104 N/m$^2$), and the lamination is preferably performed under reduced pressure such as air pressure of 20 mmHg (26.7 hPa) or less.

6. Conductive Paste

As a method of obtaining a conductive paste from the composition of the present invention, for example, a method of dispersing conductive particles in the composition can be exemplified. Depending on the kinds of conductive particles used, the conductive paste can be a circuit connection paste resin composition or an anisotropic conductive adhesive.

EXAMPLES

Next, the present invention will be specifically described with reference to examples and comparative examples. In the following description, "part" and "%" are based on mass unless otherwise specified.

Note that, $^1$H and $^{13}$C-NMR, MS spectrum and IR were measured under the following conditions.

$^1$H-NMR: measurement was performed using "JNM-ECA600" manufactured by JEOL RESONANCE.

Magnetic Field Strength: 600 MHz
Number of integrations: 16 times
Solvent: DMSO-d6
Sample concentration: 30% by mass $^{13}$C-NMR: measurement was performed using "JNM-ECA600" manufactured by JEOL RESONANCE.

Magnetic Field Strength: 150 MHz
Number of integrations: 4,000 times
Solvent: DMSO-d6
Sample concentration: 30% by mass FD-MS: measurement was performed using "JMS-T100GC AccuTOF" manufactured by JEOL Ltd.

Measurement range: m/z=50.00 to 2000.00
Change rate: 25.6 mA/min
Final current value: 40 mA
Cathode voltage: −10 kV Example 1

Synthesis of Oxazine Compound (A-1)

A four-neck flask equipped with a dropping funnel, a thermometer, a stirring device, a heating device, and a reflux condenser with cooling was charged with 198.3 g (1.0 mol) of 4,4'-diaminodiphenylmethane, and 296.4 g (2.0 mol) of 4-propargyloxyphenol with nitrogen gas flowing, the mixture was dissolved in 1,270 g of toluene, then 127.8 g (4.0 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 434.3 g of oxazine compound (A-1).

From the aspect that $^1$H-NMR indicated peaks at 7.05 ppm to 6.99 ppm (8H), 6.76 ppm to 6.62 ppm (4H), 6.62 ppm (2H), 5.27 ppm (4H), 4.59 ppm (4H), 4.55 ppm (4H), 3.78 ppm (2H), and 2.50 ppm (2H), $^{13}$C-NMR indicated peaks at 151.2 ppm, 148.7 ppm, 146.2 ppm, 134.2 ppm, 129.3 ppm, 121.1 ppm, 118.3 ppm, 117.3 ppm, 114.7 ppm, 112.7 ppm, 79.5 ppm, 78.6 ppm, 75.3 ppm, 56.3 ppm, 50.4 ppm, and 40.0 ppm, and matrix spectrum indicated a peak at $M^+$=542, it was confirmed that a desired oxazine compound (A-1) represented by the following formula was obtained.

[Chem. 37]

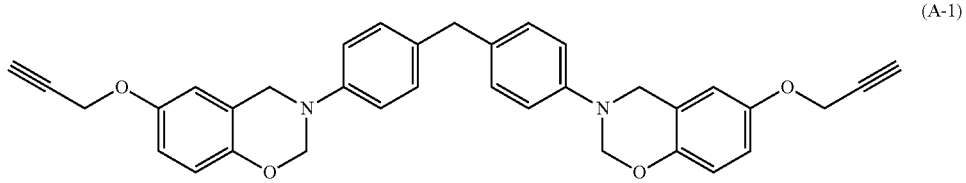

(A-1)

Example 2

Synthesis of Oxazine Compound (A-2)

A four-neck flask equipped with a dropping funnel, a thermometer, a stirring device, a heating device, and a reflux condensor with cooling was charged with 158.2 g (1.0 mol) of 1,5-diaminonaphthalene, and 296.4 g (2.0 mol) of 4-propargyloxyphenol with nitrogen gas flowing, the mixture was dissolved in 1,270 g of toluene, then 127.8 g (4.0 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 352.7 g of oxazine compound (A-2).

From the aspect that $^1$H-NMR indicated peaks at 7.88 ppm (2H), 7.41 ppm to 7.33 ppm (4H), 6.78 ppm to 6.70 ppm (6H), 5.33 ppm (4H), 4.65 ppm (8H), and 3.51 ppm (2H), $^{13}$C-NMR indicated peaks at 151.1 ppm, 147.8 ppm, 146.1 ppm, 129.3 ppm, 125.7 ppm, 121.4 ppm, 119.5 ppm, 116.9 ppm, 116.7 ppm, 114.8 ppm, 112.8 ppm, 81.1 ppm, 79.5 ppm, 78.0 ppm, 55.7 ppm, and 51.6 ppm, and matrix spectrum indicated a peak at $M^+$=502, it was confirmed that a desired oxazine compound (A-2) represented by the following formula was obtained.

Synthesis Example 1

Synthesis of Monopropargyl Ether-Containing Mixture (C-1)

A four-neck flask equipped with a dropping funnel, a thermometer, a stirring device, a heating device, and a reflux condensor with cooling was charged with 400.0 g (2.1 mol) of 4,4'-biphenol and 3,000 mL of dehydrated THF with nitrogen gas flowing, and the mixture was stirred and dissolved. While maintaining the reaction solution at 10° C. or less, 43.0 g (1.1 mol) of sodium hydride (60%, dispersed in liquid paraffin) was added in portions over one hour. After returning to room temperature over one hour, the temperature was raised to set a reflux state. Under reflux, 159.7 g (1.1 mol) of propargyl bromide (80% toluene solution) was added dropwise over one hour. After completion of the dropwise addition, the reaction was performed under reflux for 24 hours.

After cooling to room temperature, sodium bromide was removed by filtration, and THF and toluene were removed under reduced pressure. 2,000 g of ethyl acetate was added to the residue to dissolve, and then was washed with alkali three times using 1,200 g of 10% aqueous sodium hydroxide solution. Subsequently, washing was performed twice with 1,800 g of ion-exchanged water. Sodium sulfate was added for drying, and then ethyl acetate was removed by filtration under reduced pressure. Vacuum drying was performed at 60° C. for 12 hours so as to obtain 98.7 g of a milky white solid (C-1). $^1$H-NMR indicated peaks at 9.44 ppm (1H), 7.51 ppm to 7.40 ppm (4H), 7.01 ppm (2H), 6.81 ppm (2H), 4.80 ppm (2H), and 3.55 ppm (1H), and $^{13}$C-NMR peaks at 156.6 ppm, 156.0 ppm, 133.5 ppm, 130.6 ppm, 127.3 ppm, 126.9 ppm, 115.6 ppm, 115.5 ppm, 115.2 ppm, 79.3 ppm, 78.1 ppm, and 55.4 ppm, which was confirmed to be a mixture (C-1) containing monopropargyl ether as an objective substance.

<Composition of Mixture (C-1)>

Monopropargyl ether 81.7%

Dipropargyl ether 18.3%

HPLC area % Detection wavelength of 254 nm

[Chem. 38]

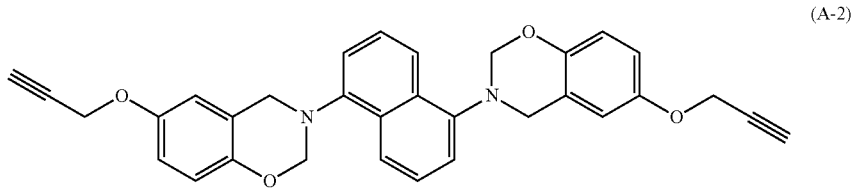

(A-2)

Synthesis Example 2

Synthesis of Dipropargyl Ether Compound (C-2)

A four-neck flask equipped with a thermometer, a cooling pipe, and a stirrer was charged with 150.2 g (0.6 mol) of 2,2-bis(3-amino-4-hydroxyphenyl) propane (BAPA, manufactured by SEIKA CORPORATION.), 1 L of DMF (N,N-dimethyl formamide), and 0.5 L of ion-exchanged water, and the mixture was stirred at room temperature. After heating the reaction solution to 60° C., 148.2 g (1.5 mol) of acetic anhydride was slowly added dropwise. After completion of the dropwise addition, the mixture was allowed to react at 60° C. for two hours and then air-cooled to room temperature. The precipitate was filtered, washed with 2 L of ion exchange water, and vacuum dried at 80° C. for ten hours so as to obtain 177.2 g of solid reaction product (d-1).

[Chem. 39]

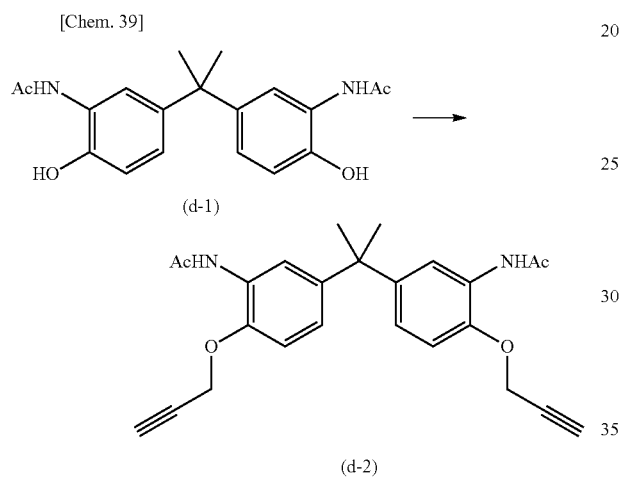

A four-neck flask equipped with a thermometer, a cooling pipe, and a stirrer was charged with 150.0 g (0.4 mol) of reaction product (d-1) and 2.2 L of acetone, and the mixture was stirred. Next, 133.8 g (1.0 mol) of potassium carbonate was added, and the reaction solution was heated to set a reflux state. After refluxing for one hour, 146.6 g (1.0 mol) of propargyl bromide (80% toluene solution) was added dropwise over 1 hour. After completion of the dropwise addition, the reaction was performed under reflux for 12 hours, and then the resultant was air-cooled to room temperature. After filtration, the reaction solution was concentrated under reduced pressure and further vacuum dried at 80° C. for ten hours so as to obtain 174.2 g of reaction product (d-2).

A four-neck flask equipped with a thermometer, a cooling pipe, and a stirrer was charged with 170.0 g (0.4 mol) of reaction product (d-2) and 330 mL of ethanol and the mixture was stirred. 108.9 g of concentrated hydrochloric acid was added thereto and the mixture was heated to 60° C. After reaction was performed at 60° C. for 30 hours, the resultant was air-cooled to room temperature. The reaction solution was neutralized with a 20% aqueous solution of sodium hydroxide and extracted with 400 mL of ethyl acetate. The extracted solution was washed twice with 200 mL of ion-exchanged water, dried over sodium sulfate added thereto, and concentrated under reduced pressure. The obtained reaction product was vacuum-dried at 80° C. for ten hours so as to obtain 129.1 g of liquid reaction product (C-2).

[Chem. 40]

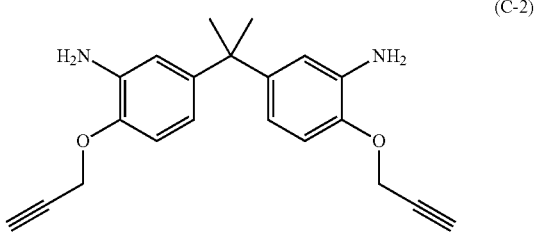

Synthesis Example 3

Synthesis of Dipropargyl Ether Compound (C-3)

[Chem 41]

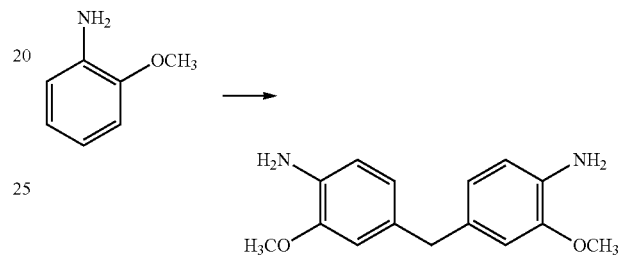

4,4'-methylenebis (2-methoxyaniline) was synthesized according to the method described in a document of Proceedings of the National Academy of Sciences, India, Section A: Physical Sciences, 71 (1), 5-12; 2001.

Synthesis of 5,5'-Methylenebis (2-Aminophenol)

[Chem. 42]

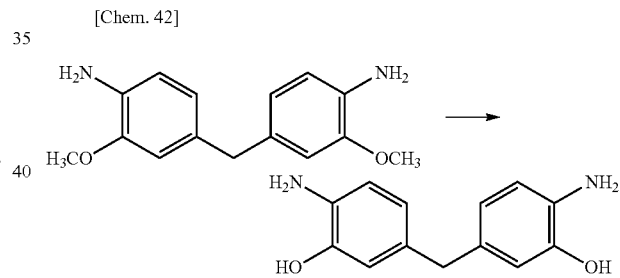

A four-neck flask equipped with a thermometer, a cooling pipe, and a stirrer was charged with 60.0 g (0.2 mol) of 4,4'-methylenebis (2-methoxyaniline), 800 mL of acetic acid, and 800 mL of hydrobromic acid (47%), and the mixture was heated to set a reflux state with stirring. After reaction was performed under reflux for 12 hours, the resultant was air-cooled to room temperature. The reaction solution was neutralized with a 20% aqueous solution of sodium hydroxide and extracted with 600 mL of ethyl acetate. The extracted solution was washed three times with 200 mL of ion-exchanged water, dried over sodium sulfate added thereto, and concentrated under reduced pressure, thereby obtaining 43.0 g of 5,5'-methylenebis (2-aminophenol).

[Chem. 43]

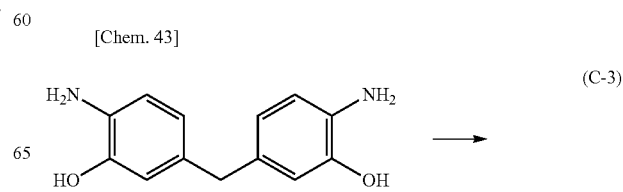

-continued

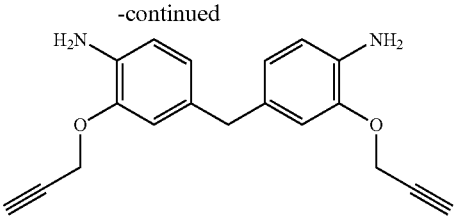

41.7 g of dipropargyl ether compound (C-3) was obtained by performing the same operation as in Synthesis Example 2 except that 2,2-bis(3-amino-4-hydroxyphenyl) propane (BAPA, manufactured by SEIKA CORPORATION.) was changed to 5,5'-methylenebis (2-aminophenol).

[Chem. 44]

Example 3

Synthesis of Oxazine Compound (A-3)

A four-neck flask equipped with a dropping funnel, a thermometer, a stirring device, a heating device, and a reflux condensor with cooling was charged with 60.0 g of the dipropargyl ether compound (C-2) and 59.3 g (0.4 mol) of 4-propargyloxyphenol with nitrogen gas flowing, the mixture was dissolved in 230 g of toluene, then 25.6 g (0.8 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 105.8 g of oxazine compound (A-3).

From the aspect that a matrix spectrum indicated a peak at $M^+=678$, it was confirmed that a desired oxazine compound (A-3) represented by the following formula was obtained.

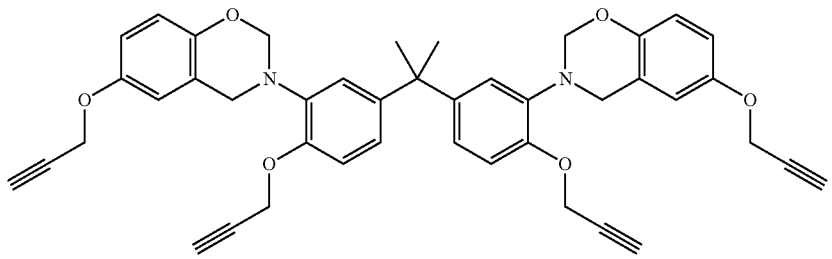

(A-3)

Example 4

Synthesis of Oxazine Compound (A-4)

A four-neck flask equipped with a dropping funnel, a thermometer, a stirring device, a heating device, and a reflux condensor with cooling was charged with 20.0 g of the dipropargyl ether compound (C-2), and 32.9 g of the monopropargyl ether-containing mixture (C-1) with nitrogen gas flowing, the mixture was dissolved in 120 g of toluene, then 7.6 g (0.2 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 26.3 g of oxazine compound (A-4).

From the aspect that a matrix spectrum indicated a peak at $M^+=830$, it was confirmed that a desired oxazine compound (A-4) represented by the following formula was obtained.

[Chem. 45]

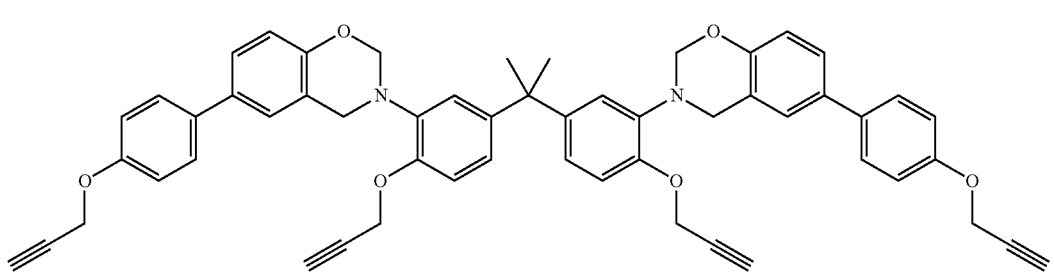

(A-4)

Example 5

Synthesis of Oxazine Compound (A-5)

A four-neck flask equipped with a dropping funnel, a thermometer, a stirring device, a heating device, and a reflux condensor with cooling was charged with 18.9 g of the dipropargyl ether compound (C-3), and 32.9 g of the monopropargyl ether-containing mixture (C-1) with nitrogen gas flowing, the mixture was dissolved in 100 g of toluene, then 7.9 g (0.2 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 23.9 g of oxazine compound (A-5).

From the aspect that a matrix spectrum indicated a peak at $M^+=802$, it was confirmed that a desired oxazine compound (A-5) represented by the following formula was obtained.

[Chem. 46]

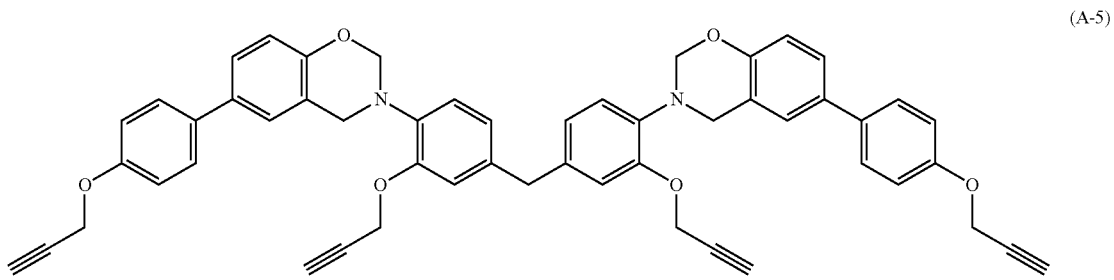

(A-5)

Example 6

Synthesis of Oxazine Compound (A-6)

A four-neck flask equipped with a dropping funnel, a thermometer, a stirring device, a heating device, and a reflux condensor with cooling was charged with 11.6 g (0.05 mol) of 2,2'-dimethyl-4,4'-diaminobiphenyl (m-TB-HG, manufactured by by SEIKA CORPORATION.) and 30.0 g of the monopropargyl ether-containing mixture (C-1) with nitrogen gas flowing, the mixture was dissolved in 90 g of toluene, then 7.0 g (0.21 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 11.6 g of oxazine compound (A-6).

From the aspect that a matrix spectrum indicated a peak at $M^+=708$, it was confirmed that a desired oxazine compound (A-6) represented by the following formula was obtained.

[Chem. 47]

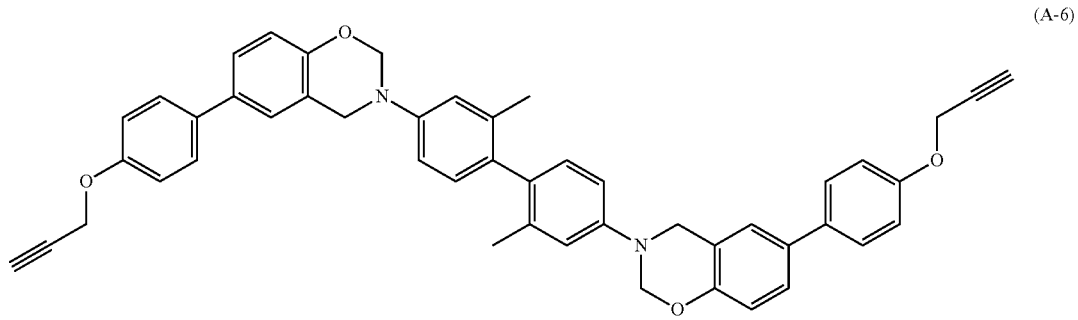

(A-6)

Comparative Synthesis Example 1

Synthesis of Oxazine Compound (B-1)

A four-neck flask equipped with a dropping funnel, a thermometer, a stirring device, a heating device, and a reflux condensor with cooling was charged with 158.2 g (1.0 mol) of 1,5-diaminonaphthalene, and 188.2 g (2.0 mol) of phenol with nitrogen gas flowing, the mixture was dissolved in 920 g of toluene, then 127.8 g (4.0 mol) of 94% paraformaldehyde was added thereto, the temperature was raised to 80° C. while stirring, and a reaction was performed at 80° C. for 7 hours. After the reaction, the resultant was transferred to a separating funnel, and an aqueous layer was removed. Thereafter, the solvent was removed from the organic layer by heating under reduced pressure so as to obtain 276 g of oxazine compound (B-1).

From the aspect that $^1$H-NMR indicated peaks at 7.89 ppm (2H), 7.41 ppm (2H), 7.34 ppm (2H), 7.12 ppm (2H), 7.02 ppm (2H), 6.87 ppm to 6.77 ppm (4H), 5.37 ppm (4H), and 4.62 ppm (4H), $^{13}$C-NMR indicated peaks at 153.5 ppm, 146.1 ppm, 129.4 ppm, 127.7 ppm, 127.1 ppm, 125.7 ppm, 121.0 ppm, 120.6 ppm, 119.5 ppm, 116.8 ppm, 116.3 ppm, 81.2 ppm, and 51.4 ppm, and a matrix spectrum indicated a peak at M$^+$=394, it was confirmed that a desired oxazine compound (B-1) represented by the following formula was obtained.

[Chem. 48]

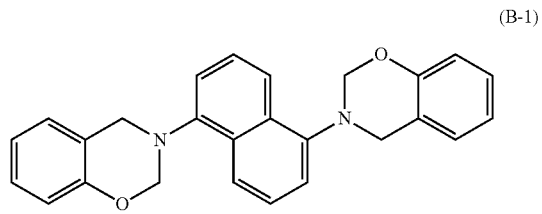

(B-1)

Examples 7 to 12 and Comparative Examples 1 to 3

Preparation of Composition and Molded Product

Each of the oxazine compounds (A-1, A-2, A-3, A-4, A-5, A-6, and B-1) obtained in Examples 1 to 6 and Comparative Synthesis Example 1, Comparative dihydrooxazine compound 1 ("F-a type benzoxazine" (reaction product of bisphenol F and formalin and aniline), manufactured by SHIKOKU CHEMICALS CORPORATION.), a comparative dihydrooxazine compound 2 ("P-d type benzoxazine" (reaction product of 4,4'-diaminodiphenylmethane, formalin, and phenol), manufactured by SHIKOKU CHEMICALS CORPORATION.), and a phenol resin ("TD-2131", phenol novolac resin manufactured by DIC Corporation) were mixed at a ratio indicated in Table 1 so as to prepare a composition.

The compositions each was subjected to the following conditions to prepare a cured product.

<Cured Product>

Curing conditions: After two hours at 170° C., two hours at 200° C., further heat cured at 250° C. for 2 hours Thickness after molding: 2.4 mm With respect to the cured products, physical properties were evaluated by the following method. The results are shown in Tables 1 to 3.

<Glass Transition Temperature>

A cured product having a thickness of 2.4 mm was cut into a size of 5 mm in width and 54 mm in length, and this was used as a test piece. The temperature at which the elastic modulus change of the test piece reached a maximum (tan δ change rate was the largest) was evaluated as the glass transition temperature by using a viscoelasticity measuring device (DMA: solid viscoelasticity measuring device "DMS 7100" manufactured by Hitachi High-Tech Science Co., Ltd., deformation mode: bifurcated bending, measurement mode: sinusoidal vibration, frequency of 1 Hz, and heating rate of 3° C./min).

TABLE 1

| | | Example 7 | Example 8 | Example 9 | Example 10 | Example 11 | Example 12 |
|---|---|---|---|---|---|---|---|
| Composition | | 1 | 2 | 3 | 4 | 5 | 6 |
| A-1 | g | 20 | | | | | |
| A-2 | g | | 20 | | | | |
| A-3 | g | | | 20 | | | |
| A-4 | g | | | | 20 | | |
| A-5 | g | | | | | 20 | |
| A-6 | g | | | | | | 10 |
| TD-2131 | g | 0.2 | 0.2 | 0.2 | 0.2 | 0.2 | 0.1 |
| Cured product | | 1 | 2 | 3 | 4 | 5 | 6 |
| Evaluation of physical properties | | | | | | | |
| Glass transition temperature Tg (DMA) | ° C. | 324 | 360< | 360< | 360< | 360< | 360< |

TABLE 2

| | | Comparative Example 1 Ratio 1 | Comparative Example 2 Ratio 2 | Comparative Example 3 Ratio 3 |
|---|---|---|---|---|
| Composition | | | | |
| B-1 | g | 20 | | |
| F-a type benzoxazine | g | | 20 | |
| P-d type benzoxazine | g | | | 20 |
| TD-2131 | g | 0.2 | 0.2 | 0.2 |
| Cured product Evaluation of physical properties | | | | |
| Glass transition temperature Tg (DMA) | ° C. | 203 | 171 | 226 |

<Thermal Decomposition Resistance>

The cured products 1 to 6 obtained in Examples 7 to 12 were finely cut and a measurement was performed in a nitrogen atmosphere at a heating rate of 5° C./min using a thermogravimetric analyzer ("TG/DTA 6200" manufactured by SII NanoTechnology Inc.), and the temperature (Td5) at which the 5% by weight decreases was determined.

<Thermal Expansion Coefficient>

The cured products 1 to 6 obtained in Examples 7 to 12 were each cut into a size of 5 mm in width and 5 mm in length and used as a test piece. This test piece was measured for the expansion coefficient at 40° C. to 60° C. using a thermomechanical analyzer (TMA/SS 7100, manufactured by SII NanoTechnology Inc., heating rate: 3° C./min).

TABLE 3

| | | Example 13 | Example 14 | Example 15 | Example 16 | Example 17 | Example 18 |
|---|---|---|---|---|---|---|---|
| Cured product | | 1 | 2 | 3 | 4 | 5 | 6 |
| Evaluation of physical properties | | | | | | | |
| Thermal decomposition resistance (Td5) | ° C. | 356 | 360 | 379 | 398 | 406 | 433 |
| Thermal expansion coefficient (40° C. to 60° C.) | ppm | 44 | 39 | 36 | 35 | 37 | 40 |

INDUSTRIAL APPLICABILITY

The cured product utilizing the oxazine compound of the present invention is excellent in the thermal decomposition resistance, the dielectric properties, and the low hygroscopicity, and thus it can be suitably used for a heat-resistant member and an electronic member. In particular, it can be suitably used for a semiconductor sealing material, a circuit board, a build-up film, a build-up substrate, and the like. It can also be suitably used for a matrix resin of a fiber-reinforced resin, and is particularly suitable as a prepreg with high heat resistance.

The invention claimed is:

1. An oxazine compound comprising:
a structure which is represented by General Formula (1-1) or (1-2):

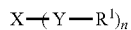 (1-1)

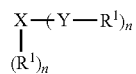 (1-2)

wherein, in Formulae (1-1) and (1-2), each n independently represents an integer of 2 to 4, each Y independently represents a structure represented by General Formula (2), X is any one of General Formulae (3), and each $R^1$ independently represents a group represented by Formula (4) or (5);

in Formula (2), a ring A represents a substituted or unsubstituted aromatic ring, and $a^1$ represents a bonding position to X in General Formula (1);

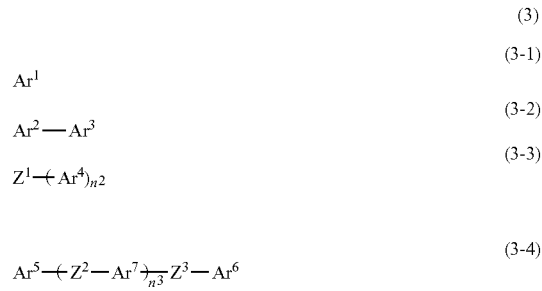

in Formula (3), $Ar^1$ to $Ar^6$ each independently represent a substituted or unsubstituted aryl group, $Ar^7$ represents a substituted or unsubstituted arylene group, $n^2$ represents an integer of 2 to 4, $n^3$ represents 1 or 2, $Z^1$, $Z^2$, and $Z^3$ each independently represent a single bond, a nitrogen atom, an oxygen atom, an alkylene group, an arylene group, a carbonyl group, an ester group, an amide group, an imino group, an azo group, a sulfide group, a sulfone group, and any one of groups obtained by combining two or more of these groups;

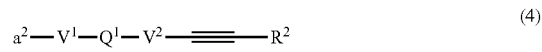

in Formula (4), $V^1$, $V^2$, and $Q^1$ each independently represent a single bond or a divalent linking group, $R^2$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^2$ represents a bonding point to General Formula (1); and

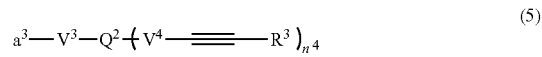

in Formula (5), $n^4$ represents an integer of 2 to 6, $V^3$ and $V^4$ each independently represent a single bond or a divalent linking group, $Q^2$ represents a linking group having a valence of $n^4+1$, $R^3$ represents a hydrogen atom, a hydrocarbon group, or a hydrocarbon group in which one or more hydrogen atoms contained in the hydrocarbon group are substituted with any one of a hydroxyl group, an alkoxy group, and a halogen atom, and $a^3$ represents a bonding point to General Formula (1).

2. The oxazine compound according to claim 1, wherein the ring A is a substituted or unsubstituted benzene ring or a substituted or unsubstituted naphthalene ring.

3. A composition comprising the oxazine compound according to claim 1.

4. The composition according to claim 3, further comprising a reactive compound.

5. The composition according to claim 3, further comprising a filler.

6. The composition according to claim 3, further comprising a fibrous substrate.

7. A cured product, which is obtained by curing the composition according to claim 3.

8. A laminate comprising:
a base material; and
a layer of the cured product according to claim 7.

9. A composition for a heat-resistant material, comprising the composition according to claim 3.

10. A heat-resistant member comprising the cured product according to claim 7.

11. A composition for an electronic material, comprising the composition according to claim 3.

12. An electronic member comprising the cured product according to claim 7.

13. A semiconductor sealing material comprising the composition according to claim 3.

14. A prepreg comprising the composition containing a fibrous substrate according to claim 6.

15. A circuit board further comprising the prepreg according to claim 14 and a copper foil layer.

16. The laminate according to claim 8, which is a build-up film.

17. A build-up substrate comprising the build-up film according to claim 16.

* * * * *